(12) United States Patent
Fessler et al.

(10) Patent No.: US 8,153,006 B1
(45) Date of Patent: Apr. 10, 2012

(54) ANAEROBIC TREATMENT PROCESS FOR ETHANOL PRODUCTION

(75) Inventors: Eric Fessler, Brookfield, WI (US); Nicholas Vollendorf, New Berlin, WI (US); Mark Pronley, Wauwatosa, WI (US)

(73) Assignee: Procorp Enterprises, LLC, Milwaukee, WI (US)

( * ) Notice: Subject to any disclaimer, the term of this patent is extended or adjusted under 35 U.S.C. 154(b) by 384 days.

(21) Appl. No.: 12/479,653

(22) Filed: Jun. 5, 2009

Related U.S. Application Data

(60) Provisional application No. 61/131,009, filed on Jun. 5, 2008.

(51) Int. Cl.
*C02F 3/28* (2006.01)

(52) U.S. Cl. ...................................... 210/603; 435/262.5

(58) Field of Classification Search .................. 210/603, 210/612; 435/262, 262.5
See application file for complete search history.

(56) References Cited

U.S. PATENT DOCUMENTS

| | | |
|---|---|---|
| 1,617,014 A | 2/1927 | Derleth |
| 3,040,060 A | 6/1962 | Kulik |
| 3,397,140 A | 8/1968 | Dea |
| 3,784,457 A | 1/1974 | Mizutani et al. |
| 4,001,198 A | 1/1977 | Thomas |
| 4,311,721 A | 1/1982 | Yoshizawa et al. |
| 4,389,317 A | 6/1983 | Trentelman et al. |
| 4,415,452 A | 11/1983 | Heil et al. |
| 4,424,275 A | 1/1984 | Levy |
| 4,501,664 A | 2/1985 | Heil et al. |
| 4,503,154 A | 3/1985 | Paton |
| 4,568,643 A | 2/1986 | Levy |
| 4,594,466 A | 6/1986 | Reeves |
| 4,595,659 A | 6/1986 | Roland et al. |
| 4,613,339 A | 9/1986 | Gunnerman et al. |
| 4,617,861 A | 10/1986 | Armstrong |
| 4,703,007 A | 10/1987 | Mulholland et al. |

(Continued)

FOREIGN PATENT DOCUMENTS

WO 02/20415 3/2002

(Continued)

OTHER PUBLICATIONS

Rana, D., et al., "Development and Characterization of Novel Hydrophilic Surface Modifying Macromolecule for Polymeric Membranes", Journal of Membrane Science, pp. 103-112, vol. 249, No. 1-2, ISSN: 0376-7388, Mar. 1, 2005.

(Continued)

*Primary Examiner* — Fred Prince
(74) *Attorney, Agent, or Firm* — Michael Best & Friedrich LLP

(57) ABSTRACT

A method of treating thin stillage from an ethanol production process that includes in a digester, treating thin stillage from the ethanol production process using anaerobic digestion to produce an ammonia-rich liquid product. During anaerobic digestion of the thin stillage, with a solids/liquids separation system of the digester, the ammonia-rich liquid product may be separated from a mixed liquor to produce a permeate. At least a portion of the permeate from the solids/liquids separation system of the digester may be recycled directly to the ethanol production process. A mesophilic anaerobic digester with a thin stillage COD loading rate of about 3 kg/m$^3$/d to at least about 7.5 kg/m$^3$d. An anaerobic biomass prepared by a method that includes subjecting the biomass to at least one stress event.

22 Claims, 19 Drawing Sheets

U.S. PATENT DOCUMENTS

| | | | |
|---|---|---|---|
| 4,812,232 A | 3/1989 | Weiss | |
| 4,916,068 A | 4/1990 | Roland et al. | |
| 4,959,237 A | 9/1990 | Walker | |
| 4,988,525 A | 1/1991 | Gresch | |
| 4,999,209 A | 3/1991 | Gnekow | |
| 5,019,135 A | 5/1991 | Sealock, Jr. et al. | |
| 5,032,265 A | 7/1991 | Jha et al. | |
| 5,126,049 A | 6/1992 | Hallberg | |
| 5,177,008 A | 1/1993 | Kampen | |
| 5,250,182 A | 10/1993 | Bento et al. | |
| 5,254,253 A | 10/1993 | Behmann | |
| 5,360,546 A | 11/1994 | Tomita et al. | |
| 5,374,356 A | 12/1994 | Miller et al. | |
| 5,399,267 A | 3/1995 | Wang et al. | |
| 5,503,750 A | 4/1996 | Russo, Jr. et al. | |
| 5,525,228 A | 6/1996 | Dague et al. | |
| 5,536,325 A | 7/1996 | Brink | |
| 5,670,047 A | 9/1997 | Burke | |
| 5,746,919 A | 5/1998 | Dague et al. | |
| 5,773,526 A | 6/1998 | Van Dijk et al. | |
| 5,798,043 A | 8/1998 | Khudenko | |
| 5,919,367 A | 7/1999 | Khudenko | |
| 6,036,854 A | 3/2000 | Potter | |
| 6,113,786 A | 9/2000 | Burke | |
| 6,126,815 A | 10/2000 | Kelada | |
| 6,187,196 B1 | 2/2001 | Way et al. | |
| 6,338,799 B1 | 1/2002 | Fukushima et al. | |
| 6,355,456 B1 | 3/2002 | Hallberg et al. | |
| 6,368,849 B1 | 4/2002 | Norddahl | |
| 6,391,207 B1 | 5/2002 | Cluyse | |
| 6,406,629 B1 | 6/2002 | Husain et al. | |
| 6,423,236 B1 | 7/2002 | Shiota et al. | |
| 6,464,875 B1 | 10/2002 | Woodruff | |
| 6,470,828 B1 | 10/2002 | Townsend et al. | |
| 6,485,645 B1 | 11/2002 | Husain et al. | |
| 6,488,854 B2 | 12/2002 | O'Leary et al. | |
| 6,514,411 B2 | 2/2003 | Pressley et al. | |
| 6,605,220 B2 | 8/2003 | Garcia et al. | |
| 6,663,777 B2 | 12/2003 | Schimel | |
| 6,676,836 B2 | 1/2004 | Mandt | |
| 6,682,578 B2 | 1/2004 | Sower | |
| 6,733,662 B2 | 5/2004 | Pollock | |
| 6,835,560 B2 | 12/2004 | Greene | |
| 6,846,343 B2 | 1/2005 | Sower | |
| 6,861,085 B2 | 3/2005 | Melwitz et al. | |
| 6,861,248 B2 | 3/2005 | Dale et al. | |
| 6,893,572 B2 | 5/2005 | Burke | |
| 6,994,782 B2 | 2/2006 | Bowers et al. | |
| 7,005,068 B2 | 2/2006 | Hoffland | |
| 7,005,072 B2 | 2/2006 | Bowers et al. | |
| 7,018,530 B2 | 3/2006 | Pollock | |
| 7,037,704 B2 | 5/2006 | Dunn-Coleman et al. | |
| 7,070,967 B2 | 7/2006 | Dale et al. | |
| 7,078,201 B2 | 7/2006 | Burmaster | |
| 7,087,170 B2 | 8/2006 | You et al. | |
| 7,102,057 B2 | 9/2006 | Lanahan et al. | |
| 7,135,116 B2 | 11/2006 | Haggerty | |
| 7,182,872 B2 | 2/2007 | Barak et al. | |
| 7,205,138 B2 | 4/2007 | Dunn-Coleman et al. | |
| 7,263,934 B2 | 9/2007 | Copeland et al. | |
| 7,267,774 B2 | 9/2007 | Peyton et al. | |
| 7,279,100 B2 | 10/2007 | Devine | |
| 7,309,602 B2 | 12/2007 | David | |
| 7,326,548 B2 | 2/2008 | Udagawa et al. | |
| 7,381,550 B2 | 6/2008 | Hallberg et al. | |
| 7,396,453 B1 | 7/2008 | Probst | |
| 7,416,644 B2 | 8/2008 | Bonde | |
| 7,498,163 B2 | 3/2009 | Greene | |
| 7,524,418 B2 | 4/2009 | Hirl | |
| 7,569,146 B2 | 8/2009 | Peyton et al. | |
| 2004/0025715 A1 | 2/2004 | Bonde et al. | |
| 2006/0194299 A1 | 8/2006 | Brinch-Pedersen et al. | |
| 2007/0119763 A1 | 5/2007 | Probst | |
| 2007/0141691 A1 | 6/2007 | Hirl | |
| 2007/0244719 A1 | 10/2007 | David | |
| 2007/0249029 A1 | 10/2007 | Marshall et al. | |
| 2007/0254089 A1 | 11/2007 | Hickey et al. | |
| 2007/0275438 A1 | 11/2007 | David | |
| 2008/0035036 A1 | 2/2008 | Bassani et al. | |
| 2008/0050800 A1* | 2/2008 | McKeeman et al. | 435/262.5 |
| 2009/0014387 A1 | 1/2009 | Probst | |
| 2010/0221804 A1* | 9/2010 | Veit et al. | 435/165 |

FOREIGN PATENT DOCUMENTS

WO     2007/008630     1/2007

OTHER PUBLICATIONS

Kaminski, Michael, D., et al., "Detoxification of Blood Using Injectable Magnetic Nanospheres: A Conceptual Technology Description", Journal of Magnetism and Magnetic Materials, pp. 398-403, vol. 293, No. 1, ISSN: 0304-8853, May 2005.

Kuhns, Sharon, "UI Investigators Evaluate Ways for Ethanol Plants to Recycle More Water", jg-tc online, available online at: <http://www.jg-tc.com/articles/2007/04/26/features/farm/doc462eaab534a73134476839.txt>, 3 pages, Apr. 25, 2007.

Cox, Ronald, "Contamination Control, Filtering Out Confusion: Select the Right Liquid Filter Media for the Right Process", Food Quality, available online at: <http://www.foodquality.com/mag/08092005/fq_08092005_CC4.html>, 5 pages, Jun. 23, 2009.

Procorp Enterprises LLC, Advancing Resource Recovery "Procorp—Expert for Sustainability Partnerships", PowerPoint Presentation, at least as early as Mar. 18, 2008.

Rein and Associates—Environmental Engineers and Operators, "Converting Thin Stillage into Renewable Energy, Fertilizer, and Recyclable Water", Phase II Report (vol. I), Nov. 18, 2007.

* cited by examiner

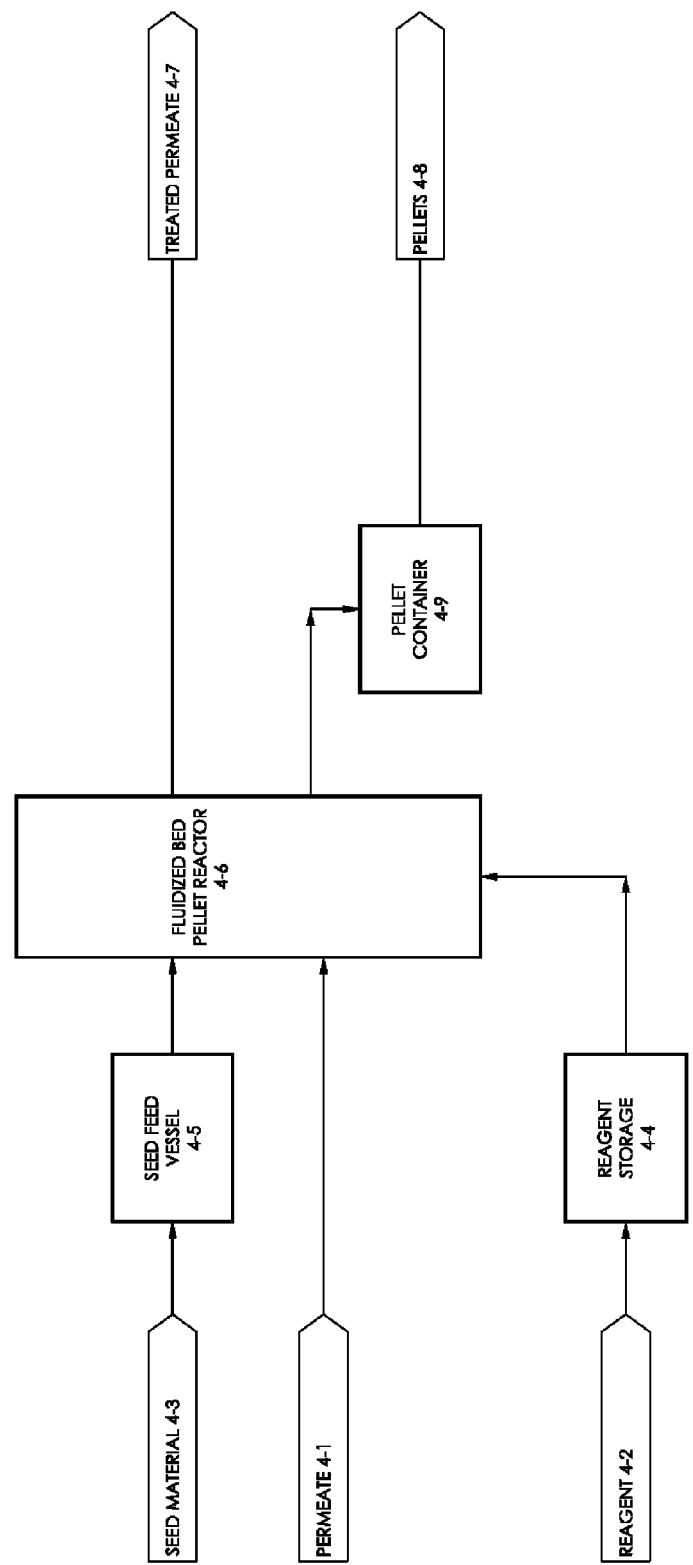

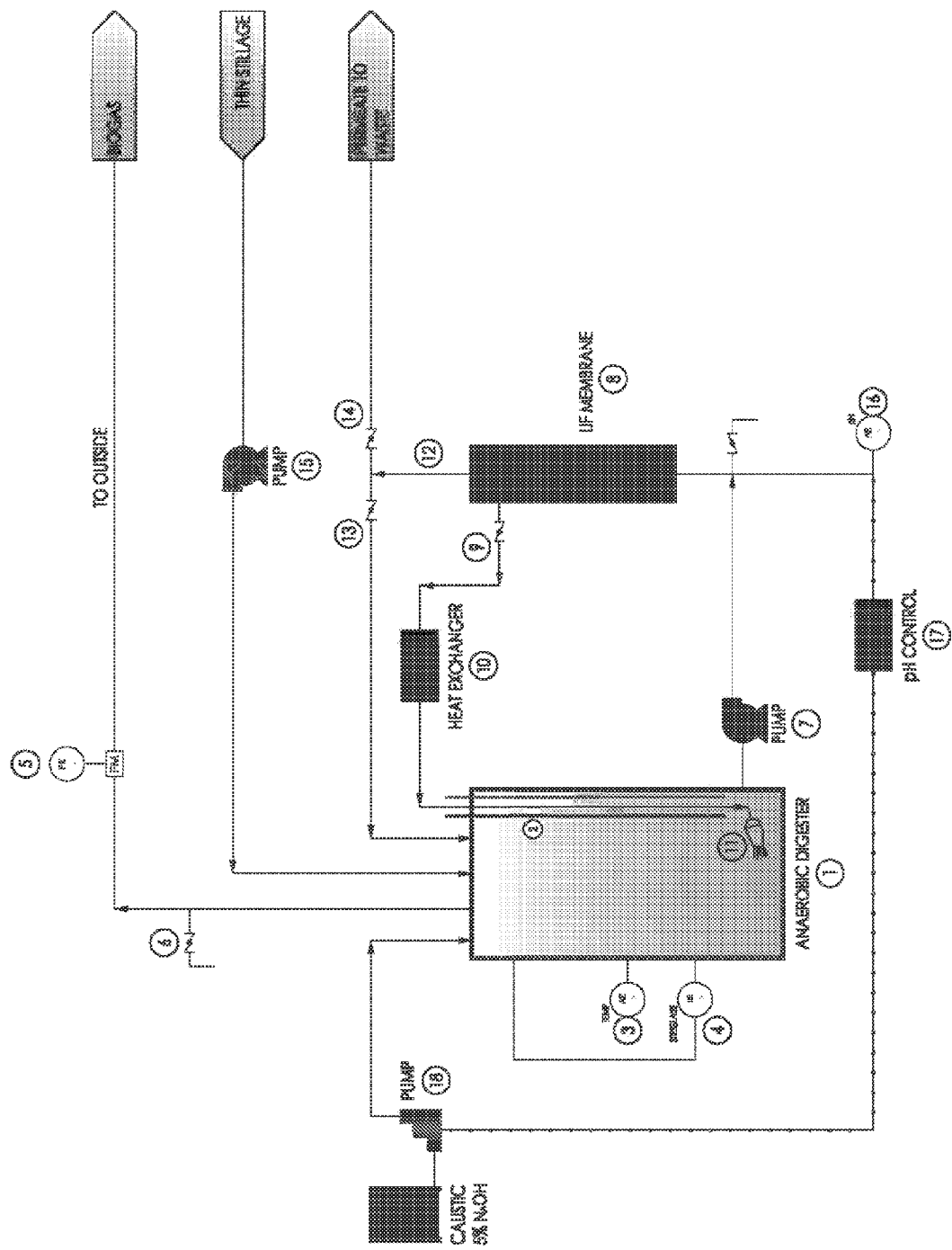

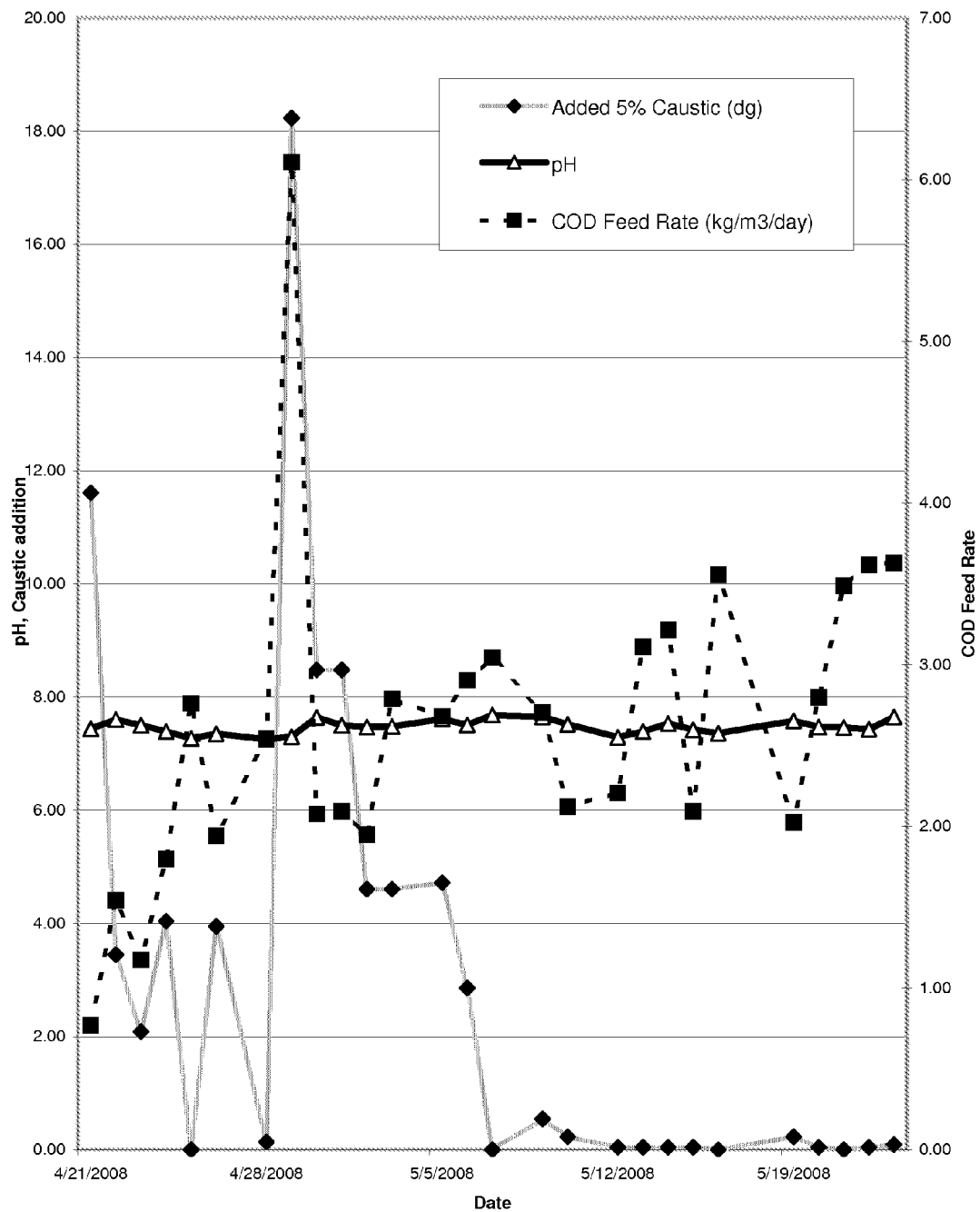

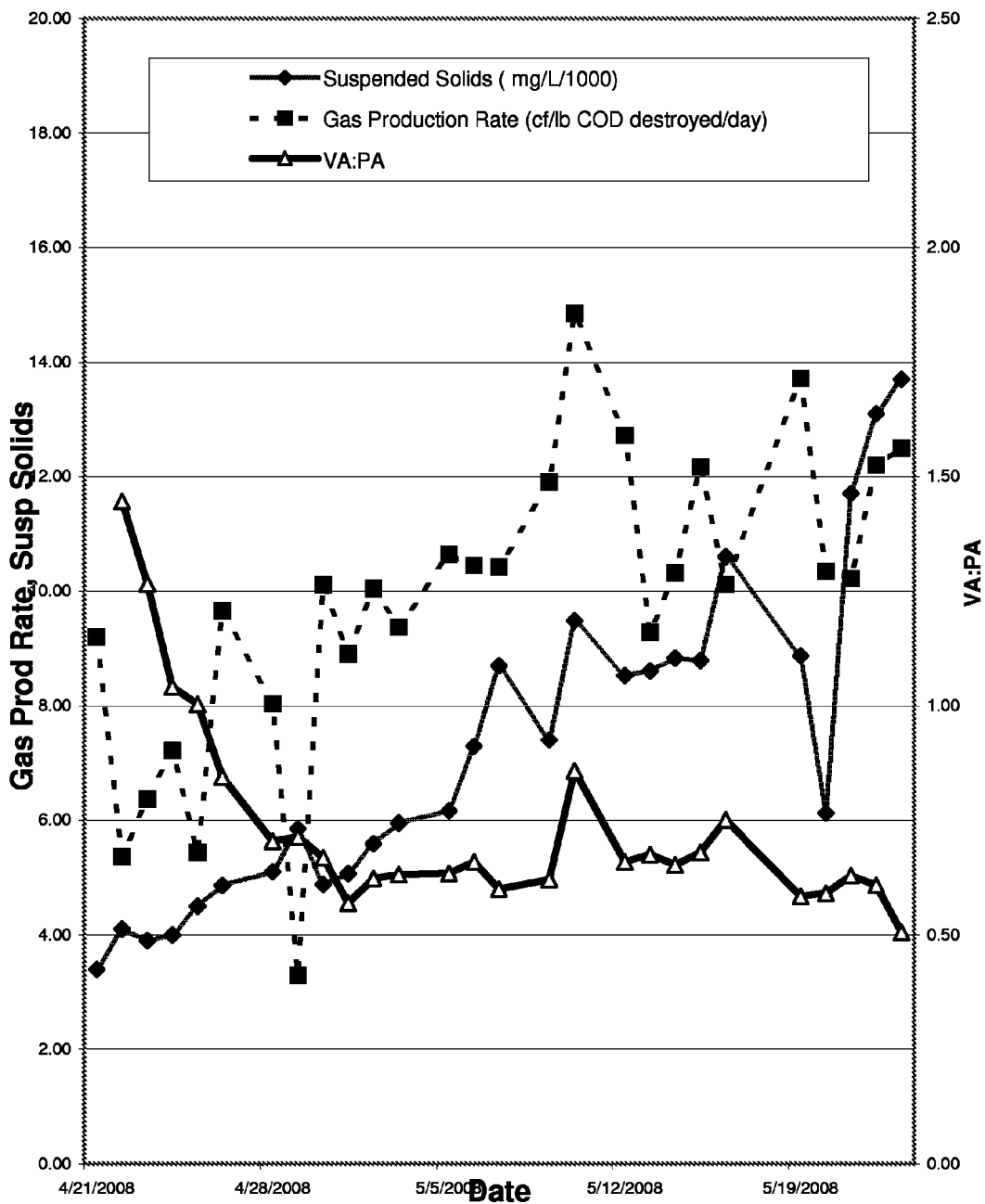

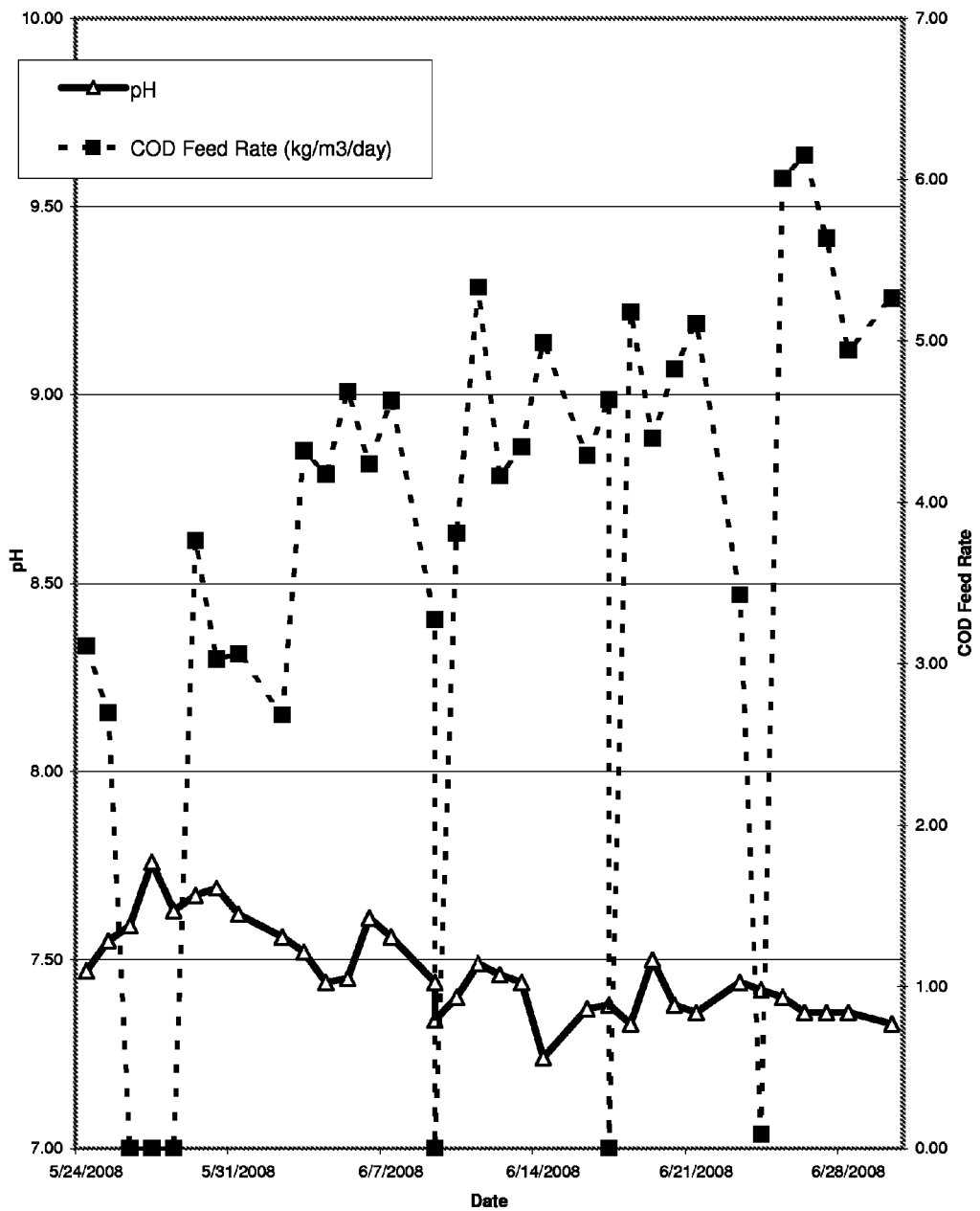
Fig 7a. Pilot Reactor Operation Biomass Building Phase 2

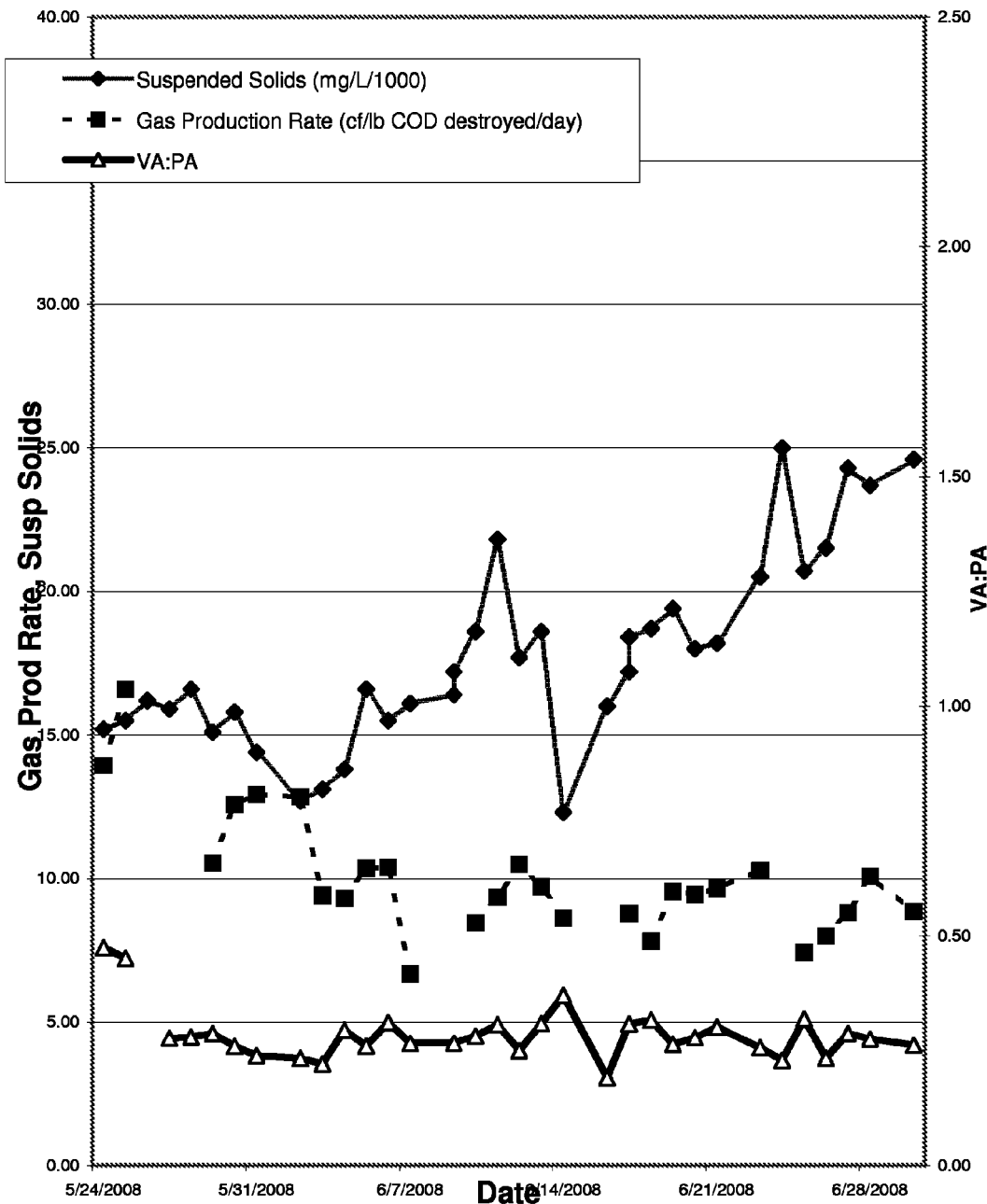
Fig 7b. Pilot Reactor Operation Biomass Building Phase 2

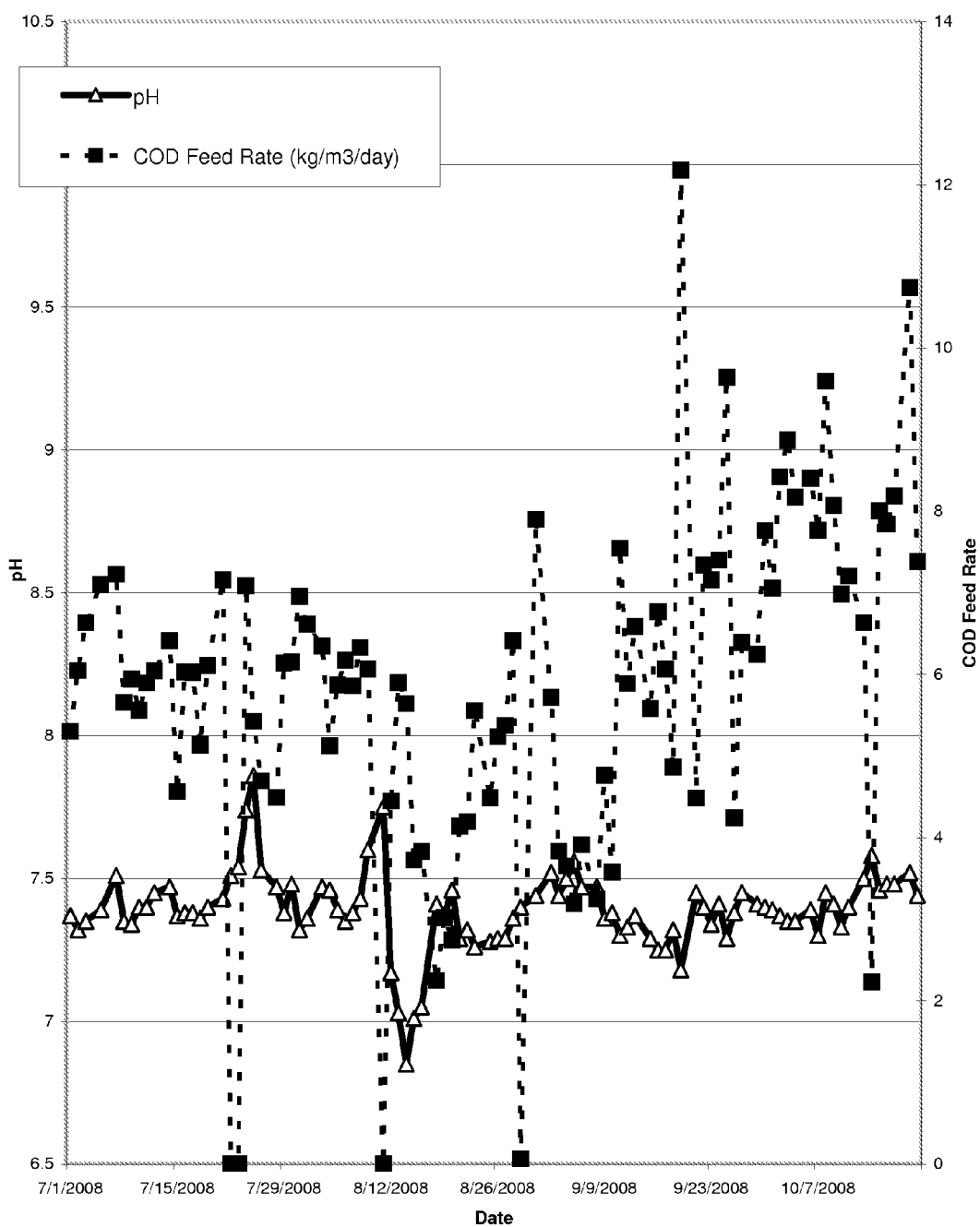
Fig 8a. Pilot Reactor: Sustained Operation

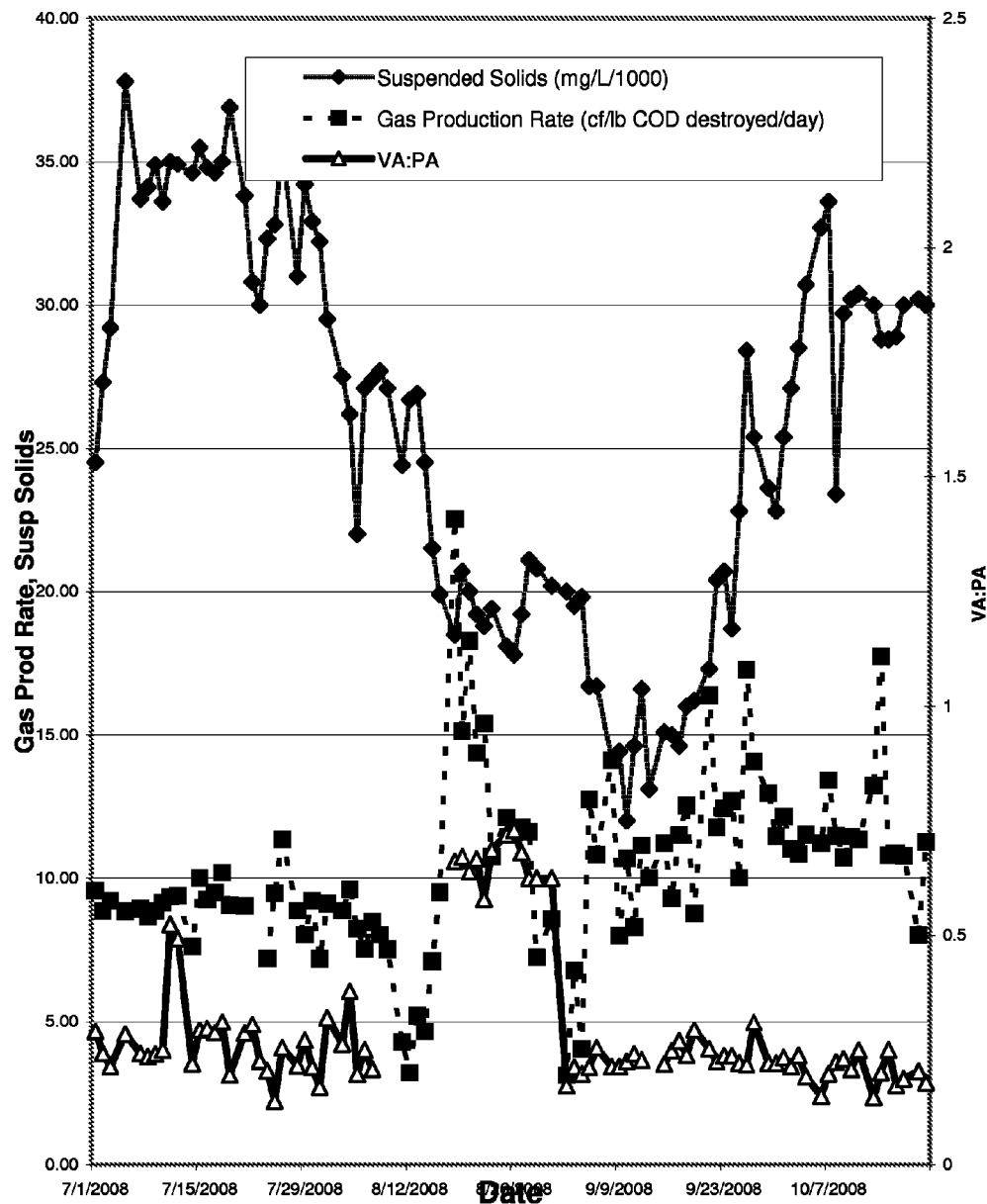
Fig 8b. Pilot Reactor: Sustained Operation

ANAEROBIC TREATMENT PROCESS FOR ETHANOL PRODUCTION

CROSS-REFERENCE TO RELATED APPLICATION

This application claims the benefit of U.S. Application Ser. No. 61/131,009, filed Jun. 5, 2008, which is incorporated by reference herein.

BACKGROUND

Ethanol production may have a significant impact on the environment through consumption of natural resources including the raw material feedstock (corn, beans, sugar cane, cellulose, etc.), energy, water, and nutrients; production of concentrated liquids; and CO2 emission. In general, ethanol production consists of feedstock preparation; liquefaction which dissolves the feedstock into solution; enzyme conversion to sugar; fermentation of the sugar into ethanol; separation of ethanol from the distillers wet grains or "whole stillage" (residual liquids and solids); and subsequent management of the whole stillage. A significant portion of the ethanol production energy and resources is spent on the management of the whole stillage.

For example, conventional corn to ethanol production (FIG. 1) involves wet or dry milling of the corn consisting of starch (60-70%), cellulose compounds (8-10%), proteins (7-9%), oil (3-4%), ash (1-2%), and water (15%). Liquefaction of the milled corn produces a suspension called corn mash. This first enzyme step involves raising the pH to 6-7, adding ammonia and urea, and adding α-amylase enzyme and heat (first 212° F.+ followed by 175-195° F.). Saccarification of the corn mash converts the starch into sugar. During the second enzyme step, the pH is lowered to 3-4 with sulfuric acid, and glucoamylase enzyme is added to convert the starch to sugar. The sugar is then converted to ethanol through fermentation with yeast (now the solution is referred to as beer). The beer is then processed through a distillation column where the ethanol is separated from the majority of the solids and water which are removed from the column as whole stillage. Distillation produces a solution which is an azeotrope of ethanol and water (95% ethanol). The azeotropic solution is then run through mole sieves to separate the ethanol from the water.

Whole stillage, in most if not all cases, is run through a solid liquid separation system (for example, a centrifuge(s)) to separate the solids (distillers' grains) from the liquid (thin stillage). Distillers' grains have feed value and are commonly dried and sold as distillers dried grains (DDG).

The thin stillage consists of remaining dissolved and suspended solids (total solids typically 5-9%) with a pH 3-4. A portion of the thin stillage typically is returned to the front of the ethanol process (backset). Backset volumes vary by plant from 20% up to 50% with periodic increases to manage accumulation of solids. The thin stillage balance conventionally is run through evaporators to produce condensed distillers' solubles or syrup.

Syrup is managed separately or is put on the DDG and sold as distillers' dried grains with solubles (DDGS). Syrup has constituents that limit the market such as fats that compromise feed quality and degradable material that generally limit the market to within 100 miles of production. The syrup market has become increasingly competitive as ethanol production (DDG and syrup supply) increases, while demand remains relatively static. Market prices have declined 2004-2007 from approximately $17-19 per ton for condensed distillers' solubles to approximately $6 per ton in Iowa.

The energy to evaporate thin stillage to syrup is substantial. Based on thermodynamics (assuming characteristics similar to water), it requires approximately 5.4 mmBTU to dry every 1,000 gallons of thin stillage from 87% moisture to 78% moisture at a 35% heat transfer efficiency. A conventional ethanol plant that produces 40-50 million gallons per year will produce approximately 575,000 gallons per day at 30% backset. The energy cost to evaporate and dry the thin stillage is equivalent to $31,000 per day in natural gas (at $10/mmBTU) and results in 66,000 tons of CO2. Ethanol plants are designed to recover as much of the heat as reasonable, however it is nonetheless a net cost to the facility that is increasing with falling syrup market price. As a result ethanol producers have implemented alternative methods to manage the thin stillage.

Alternate methods that are available in the market include thin stillage treatment to produce water quality that can be returned to the process and thin stillage evaporation and burning to capture the BTU value of the syrup. Thin stillage treatment has consisted of anaerobic digestion with nutrient removal (if required) followed by a secondary treatment of aerobic and/or membrane (reverse osmosis or nano-filtration) treatment. The anaerobic treatment process produces biogas that can be used by the facility boilers to offset natural gas purchases. The secondary treatment with aerobic and/or reverse osmosis or nano-filtration membrane separation produces water that can be returned to the process. This secondary treatment consumes substantial energy (greater than $1,000,000 annually) in the form of electrical horsepower required to power the blowers to aerate the aerobic process and oxidize the organic and nitrogen constituents and achieve the pressure (greater than 4 bar) across the membrane. In addition, waste concentrated liquids and solids, typically 250,000 gallons±50,000 gallons per day, are produced that require off-site disposal. Commonly the operating cost of these treatment systems is relatively equivalent to the energy value recovered in the biogas.

Burning the thin stillage is another alternative that has been used to capture the energy value of the organic constituents of the thin stillage. It has been reported that the solids content has to be 12.5% or greater for the heating value to be sufficient to break even with the energy required to heat and evaporate the water present. Assuming the thin stillage has a total solids content of 6-7%, one-half (50%) of the water has to be evaporated to achieve break even energy on the burner. Based on the 40-50 million gallons a year plant example, it will cost $23,000 dollars a day in natural gas and 49,000 tons of CO2 per year to burn all of the thin stillage produced.

SUMMARY

In some independent aspects and in some independent constructions, the invention may provide a method of treating thin stillage from an ethanol production process. The method may generally include in a digester, treating thin stillage from the ethanol production process using anaerobic digestion to produce an ammonia-rich liquid product. Also, during anaerobic digestion of the thin stillage, with a solids/liquids separation system of the digester, the ammonia-rich liquid product may be separated from a mixed liquor to produce a permeate. In addition, at least a portion of the permeate from the solids/liquids separation system of the digester may be recycled directly to the ethanol production process.

A secondary treatment step may not be used to treat the permeate before recycling it into the ethanol production process. The ammonia-rich liquid product may be separated from the mixed liquor using membrane technology. The ammonia-rich liquid product may be separated from the mixed liquor using at least one of microfiltration, ultrafiltration, nanofiltration, reverse osmosis, and combinations thereof. The permeate may be recycled directly to the ethanol production process as a substitute for water in one of a liquefaction step, a saccarifation step, and a combination thereof in the ethanol production process. The permeate may replace water in the ethanol production process in a range of about 1% to 100%. The permeate may replace from about 1% to about 100% of a nitrogen requirement of the ethanol production process.

A method of treating thin stillage from an ethanol production process may also include handling biogas produced during anaerobic digestion, removing solids produced during anaerobic digestion, and removing ammonia produced during anaerobic digestion including producing struvite from ammonia, and removing the struvite. Handling biogas produced during anaerobic digestion may include producing biogas, purifying the biogas to remove $H_2S$ to produce an elemental sulfur byproduct, and using the biogas for energy in the ethanol production process. The digester may have a threshold for at least one of ammonia, phosphorus, and magnesium, and the method may further include removing excess of at least one of ammonia, phosphorus, and magnesium above the threshold by processing at least a fraction of the permeate in a fluidized bed reactor to produce pellets of struvite. The threshold may be 2500 mg/L of ammonia in the digester. The method of treating thin stillage from an ethanol production process may also include providing a mixing system in the digester and mixing contents in the digester with the mixing system. The mixing step may include continuously operating the mixing system to continuously mix the contents in the digester.

In some independent aspects and in some independent constructions, the invention may provide a method for reducing energy required to treat thin stillage from an ethanol production process. A solids/liquid separation process may be combined in an anaerobic digestion process. The method may generally include, in a digester, treating thin stillage from the ethanol production process using anaerobic digestion to produce an ammonia-rich liquid product. Also, during anaerobic digestion of the thin stillage, with a solids/liquids separation system of the digester, the ammonia-rich liquid product may be separated from a mixed liquor to produce a permeate. In addition, at least a portion of the permeate from the solids/liquids separation system of the digester may be recycled directly to the ethanol production process.

In some independent aspects and in some independent constructions, the invention may generally provide a mesophilic anaerobic digester with a thin stillage COD loading rate of about 3 kg/m$^3$/d to at least about 7.5 kg/m$^3$d. The mesophilic anaerobic digester may have a thin stillage COD loading rate of at least about 6 kg/m$^3$/d. The mesophilic anaerobic digester may have a thin stillage COD loading rate of at least about 7.5 kg/m$^3$/d.

In some independent aspects and in some independent constructions, the invention may provide a method of building biomass in an anaerobic digester. At least one stress event may be employed to speed growth of biomass adapted to metabolizing thin stillage.

In some independent aspects and in some independent constructions, the invention may provide a method of building biomass in an anaerobic digester. Generally, at least one stress event may be employed to speed growth of biomass adapted to metabolizing thin stillage. Employing at least one stress event may include at least one of injecting air or oxygen into the anaerobic digester, increasing the COD loading of thin stillage beyond the standard feed rate for at least one short burst of time, spiking the anaerobic digester with an inhibitory chemical, adjusting temperature of the anaerobic digester, and adding an acid to the anaerobic digester.

In some independent aspects and in some independent constructions, the invention may generally provide an anaerobic biomass prepared by a method that includes subjecting the biomass to at least one stress event.

In some independent aspects and in some independent constructions, the invention may generally provide an anaerobic biomass prepared by a method that includes subjecting the biomass to at least one stress event. Subjecting the biomass to at least one stress event may include at least one of injecting air or oxygen into the biomass, increasing the COD loading of a waste stream to be treated beyond the standard feed rate for at least one short burst of time, spiking the biomass with an inhibitory chemical, adjusting temperature of the biomass, and adding an acid to the biomass. The anaerobic biomass may be capable of processing waste streams with a COD loading rate of at least 6 kg/m$^3$/d.

Independent features and independent advantages of the invention will become apparent to those skilled in the art upon review of the following detailed description, claims and drawings.

BRIEF DESCRIPTION OF THE DRAWINGS

FIG. 4 is a schematic illustration of a pellet reactor system for struvite removal.

FIG. 5 is a schematic illustration of a pilot anaerobic treatment process for digesting thin stillage.

FIG. 6a is a chart summarizing pilot reactor operational parameters during Biomass Building Phase 1, Example 2.

FIG. 6b is a chart summarizing additional pilot reactor operational parameters during Biomass Building Phase 1, Example 2.

FIG. 7a is a chart summarizing pilot reactor operational parameters during Biomass Building Phase 2, Example 3.

FIG. 7b is a chart summarizing additional pilot reactor operational parameters during Biomass Building Phase 2, Example 3.

FIG. 8a is a chart summarizing pilot reactor operational parameters during Sustained Operation, Example 4.

FIG. 8b is a chart summarizing additional pilot reactor operational parameters during Sustained Operation, Example 4.

Before any independent embodiments or constructions of the invention are explained in detail, it is to be understood that the invention is not limited in its application to the details of construction and the arrangement of components set forth in the following description or illustrated in the following drawings. The invention is capable of other independent embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

It also is understood that any numerical range recited herein includes all values from the lower value to the upper value. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this application.

DESCRIPTION

Figure 2:
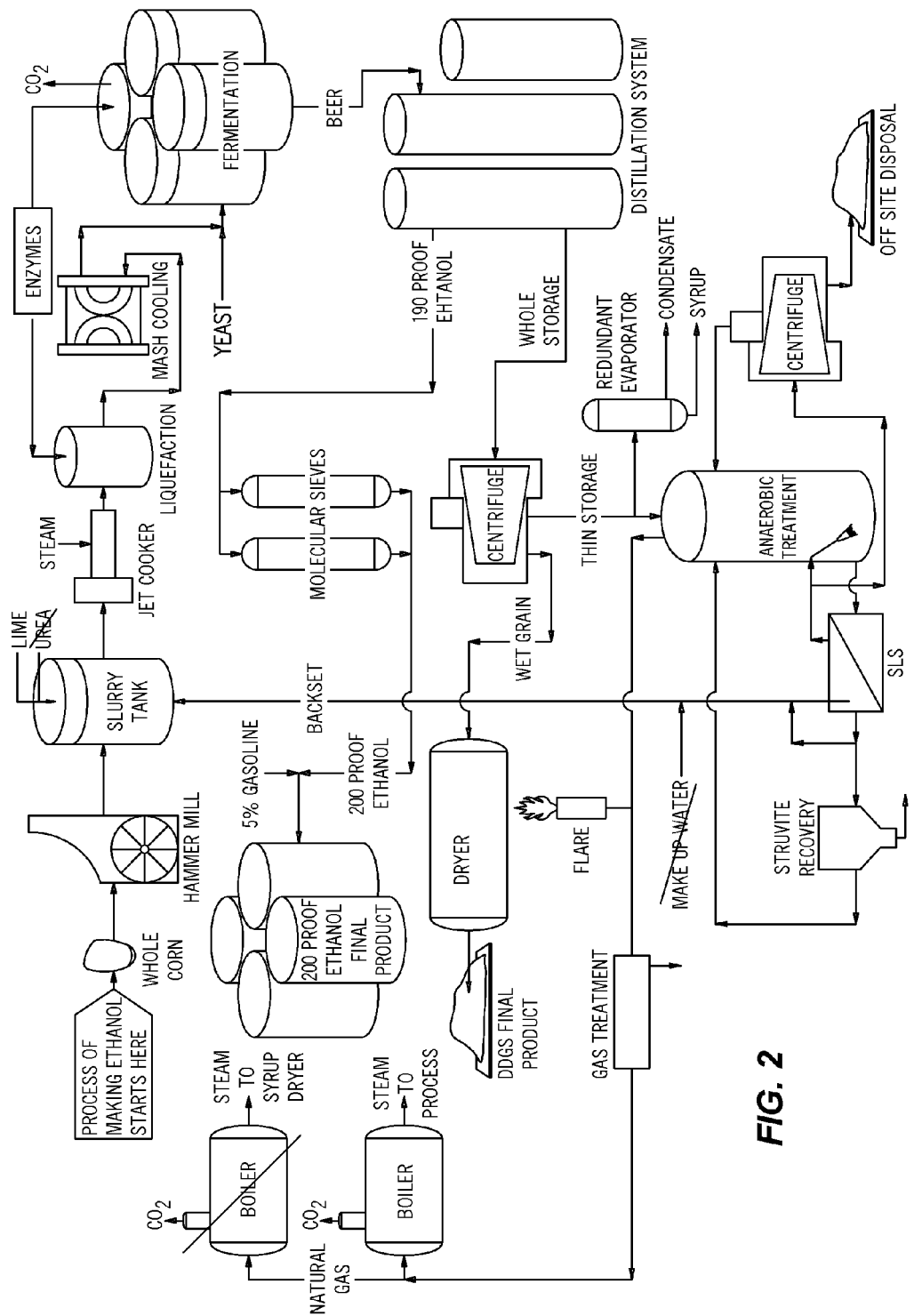
FIG. 2 is a schematic illustration of an ethanol production process and system including an anaerobic treatment process for thin stillage.

In some independent aspects and in some constructions, the present invention generally relates to a process for converting waste to nutrients and energy and may generally relate to treating thin stillage generated from ethanol production. About 100% of thin stillage generated from ethanol production (what is traditionally a returned and non-returned portion) may be processed using an anaerobic treatment process (FIG. 2). An anaerobic treatment process, such as anaerobic digestion, uses an organic destruction mechanism.

The anaerobic digestion of the thin stillage produces a liquid rich in ammonia, biogas containing a sulfur byproduct (such as $H_2S$), and solids containing the biomass responsible for anaerobic digestion (commonly referred to as sludge or biomass).

An anaerobic digestion system for thin stillage (FIG. 3) will have 5 major subsystems; these are the anaerobic digesters (3-1), a solid liquid separation system ("SLS") (3-2), a biogas handling system (3-3), solids removal system (3-4), and struvite removal system (3-5). The anaerobic digesters may be mesophilic anaerobic digesters.

The anaerobic digester subsystem (3-1) will consist of one of more air tight tanks, a mixing system, a pH control system, a temperature control system, and a foam control system.

The volume of the tanks are based on the volume and COD of thin stillage to be digested; digester capacity may be conservatively sized to allow a COD loading rate as low as about 3 or about 4 kg COD per cubic meter of digester volume ($kg/m^3$), particularly between about 5 to about 6 $kg/m^3$, more particularly about 6.5 to about 7.5 $kg/m^3$. The COD loading rate may be at least about 6 $kg/m^3$, particularly at least about 7.5 $kg/m^3$. In some embodiments, the digester may have or may develop a COD loading capacity which is greater than that required for treatment of the thin stillage from the ethanol production process. In such cases, waste from other sources outside of the ethanol production process could be added to and treated by the anaerobic digestion system. Such outside sources of waste could include at least one of bran by-product produced in corn fractionation processes, corn stover, or algae. In addition, organic material from dedicated energy crops such as at least one of switch grass, hybrid poplar, hybrid willows, sugarcane and algae, or others could be added to the anaerobic digestion system.

A mesophilic anaerobic digester may be adapted to process these COD loading rates by building biomass by employing at least one stress event to speed growth of biomass adapted to metabolizing thin stillage. The biomass may be stressed to help it adapt to become more efficient at digesting thin stillage. A stress event would be employed to stress the biomass without destroying too much of it, and any event that will stress a biomass without destroying it could be considered a stress event.

In alternative embodiments, a biomass may be built to help it adapt to become more efficient at digesting wastes other than thin stillage. Stress events may include, but are not limited to, at least one of aspirating air into the biomass, increasing the COD loading of a waste stream to be treated (such as thin stillage) beyond the standard feed rate for at least one relatively short duration of time, spiking the biomass with an inhibitory chemical, adjusting the temperature of the biomass, adding an acid to the biomass, etc.

Small amounts of air or oxygen may be injected into the biomass by adding a controlled flow rate of compressed air or oxygen to any of the liquid streams entering the digester. These liquid streams, or return streams, include the thin stillage, liquid streams as part of the mixing system (below), returned permeate and retentate from the SLS system (3-2), and liquids produced as part of the solids removal system (3-4). An indication or symptom that too much air is being added may be foaming. Increasing the COD loading of thin stillage may occur by spiking the COD loading of thin stillage for a short duration of time, and then reducing the COD loading. This may be done once or multiple times, with varying sizes of COD spiking. Another indication of stress is the alkalinity ratio, volatile acid alkalinity (VA) to partial alkalinity (PA). Stress events should be terminated before this VA:PA ratio increases by about 2× the value prior to stressing. Sufficient time should be allowed for this ratio to recover before subjecting the biomass to another stress event.

During startup the digesters may be seeded with biomass (from other anaerobic digesters) adapted to the anaerobic digestion of organic material. In some embodiments the source of biomass may be anaerobic digesters such as those in municipal waste water treatment plants or digesters used to treat high strength industrial waste water such as at food processing plants. In other embodiments, the biomass source may be anaerobic digesters used to treat wastewater at dairy and cheese processing plants. In order to avoid the potential risks from human pathogens, in some embodiments, the biomass source will not be from a municipal waste water treatment plant.

The biomass may be built up in the digesters by starting with the biomass seed and building it to grow to about 3% suspended solids. Biomass concentrations should be maintained between about 15,000 to about 50,000 mg/L (about 1.5 to 5.0%), particularly between about 20,000 to about 40,000 mg/L, and more particularly between about 25,000 to about 35,000 mg/L (about 2.5 to 3.5%). During build-up, thin stillage, micronutrients, iron (as an iron chloride solution) and VitaStim (commercial supplement by Aquafix, Madison, Wis.) may be added to the digester. This supplementation may occur continuously or intermittently. Supplementation may also occur intermittently, continuously, or initially and then cease during sustained operation of an anaerobic digester. pH control may or may not be used during build-up of the biomass.

The mixing system may include a series of jets in the bottom of the tanks; liquid flowing through the jets keeps suspended solids in the digesters from settling and blends the mixed liquor with the thin stillage entering the tanks. The number and size of the jets will depend on the tanks size; they may be supplied entirely or in part with the same pumping system used in the SLS. For larger tanks it may be necessary to use additional pumps dedicated to circulating digester mixed liquor though the jets. The mixing in the anaerobic digester may be continuous or intermittent.

The pH control system consists of a pH monitoring system which provides feedback to a basic or caustic supply system which dispenses base or caustic to the digester, as needed, to maintain pH above the set-point. The pH control system will maintain the pH in the digester at values between pH about 6 to about 8, particularly between about 6.8 and about 7.5, and more particularly between about 7.2 and about 7.3.

The temperature control system consists of a temperature monitoring system which provides feedback to a heat exchanger system; because thin stillage may be hot as it enters the digester, the heat exchanger may remove heat from the digester. This heat may be recycled and reused. Alternatively, the thin stillage may be cool as it enters the digester and may need to be heated. The temperature control system will maintain the digester temperature between about 88 and about 98 degrees Fahrenheit, particularly between about 90 and about 96 degrees, and more particularly between about 93 and about 95 degrees.

Foam may be monitored using an ultrasonic foam level sensor. Antifoamant chemicals may be added to the anaerobic digesters as needed to reduce the foam level to avoid operational issues (i.e., foam in biogas piping).

During anaerobic digestion of thin stillage a solid liquid separation subsystem ("SLS") may be employed to separate the ammonia rich liquid product from the bulk digester suspension (commonly referred to as mixed liquor) (3-2). The SLS may include, but is not limited to, membrane technology. For example, without limitation, the membrane technology can be at least one of microfiltration, ultrafiltration, nanofiltration, reverse osmosis, and combinations thereof. Examples of anaerobic/SLS systems may be found in co-owned U.S. Pat. No. 7,396,453 and co-owned, co-pending U.S. Publication No. 2009/0014387, the entire contents of which are hereby fully incorporated by reference. The capacity of the SLS system must be capable of maintaining a constant level in the digesters, therefore it must be capable of removing a volume per day of permeate approximately equal to the volume per day of thin stillage added to the digesters. The percentage of permeate removed from the total volume of liquid circulated through the SLS system will be between about 1% and about 25%, particularly between about 2% and about 12%, more particularly between about 4% and about 6%. Retentate from the SLS may be returned to the digester.

The separated ammonia rich liquid product (commonly referred to as permeate if produced using membrane technology) may be of sufficient quality that it may be used as a substitute for water in the liquefaction and/or saccarification steps of the ethanol production process. The separated ammonia rich liquid product may be returned to the ethanol production process without the need for secondary treatment. This may reduce energy consumed and waste produced. The ammonia concentration in this liquid will be between about 200 mg/L and about 3000 mg/L, particularly between about 800 mg/L and about 2500 mg/L. This ammonia present in the water may replace the need to add ammonia and urea during the liquefaction step. Permeate may be substituted in the range of about 1% to about 100% replacement of the water, particularly about 50% to about 100%, more particularly about 85% to about 100%. Depending on the substitution level of permeate and it's ammonia concentration, the permeate may replace from about 1-100% of the nitrogen (ammonia and urea) requirement of the ethanol production process. This substitution may off-set raw material costs normally required for liquefaction. The permeate may have a pH ranging from about 6-8, which may reduce or change the pH adjustments needed for optimal liquefaction.

The biogas handling subsystem (3-3) will include a biogas collection system, biogas drying system, and a hydrogen sulfide treatment system; in some embodiments the biogas handling subsystem may also include a biogas compression system. In some embodiments, the biogas collection system may be incorporated into the covers of the anaerobic digesters. The system should be sized to handle biogas volumes of between about 3 and about 15 cubic feet per pound of chemical oxygen demand destroyed ($ft^3$/lbCOD), particularly between about 6 and about 12 $ft^3$/lbCOD, and more particularly between about 8 and about 10 $ft^3$/lbCOD. This biogas may be comprised of about 40-60% methane, about 40-60% carbon dioxide and trace constituents, like water and $H_2S$ at levels ranging from about 1000-10,000 ppm. Biogas, after drying and removal of the $H_2S$, may be burned for most or all applications in which natural gas would traditionally be burned. These applications will be apparent to those skilled in the art. They include, but are not limited to, combustion to provide heat to the ethanol facility boilers and fuel for internal combustion engine gensets to produce electricity. In other embodiments, the biogas may be compressed prior to use or sale. In other embodiments, part or all of the $CO_2$ may be separated from the methane prior to use or sale. Given the COD content and quantities of thin stillage produced as a result of ethanol production, this biogas could offset natural gas purchases by the ethanol production plant worth millions of dollars per year.

The purification of biogas by removal of $H_2S$, may in some aspects result in an elemental sulfur byproduct. Methods for removal of $H_2S$ from biogas by conversion to elemental sulfur are well known to those skilled in the art. The elemental sulfur from such a purification process may have value as a commodity.

The solids removal system (3-4) will include equipment to separate biosolids, or biomass, from the digester contents. Liquid produced by the solids removal system may be returned to the digester. This equipment is necessary to control the concentration of biomass in the digesters. Measurement of suspended solids is used an estimate of the biomass concentration. Biomass concentrations should be maintained between about 15,000 to about 50,000 mg/L (about 1.5 to 5.0%), particularly between about 20,000 to about 40,000 mg/L, and more particularly between about 25,000 to about 35,000 mg/L (about 2.5 to 3.5%). In some independent embodiments, the biosolids removal equipment may be, but is not limited to, centrifugation equipment. In some embodiments, this equipment may directly process mixed liquor from the digester. In other embodiments, this equipment may process retentate from the SLS system. The biomass removed from the system may have a moisture content ranging from about 50-80%, particularly about 50-60%.

In some independent aspects and in some constructions, an ammonia control system may be used to prevent ammonia from building up in the anaerobic digester where it is inhibitory at levels greater than about 3000 mg/L. The anaerobic digestion of thin stillage may, over time, produce an excess, even inhibitory level, of ammonia in the digester. This excess ammonia may be combined with phosphate and magnesium, also released by the anaerobic digestion process, to precipitate struvite, and, in one embodiment, the present invention may include a struvite removal subsystem (3-5). In some embodiments, the equipment for removal of ammonia, phosphorus and magnesium will be operated to maintain an ammonia concentration in the anaerobic digester of less than about 3000 mg/L, and more particularly between about 800 mg/L and about 2500 mg/L. In some embodiments, the ammonia concentration in the anaerobic digester should be less than about 3000 mg/L.

When or before the level of ammonia in the digester exceeds this threshold, excess ammonia may be removed/treated so that the level of ammonia does not continue to build up in the digester and/or so the excess amount is not returned to the ethanol production process and, thus, does not return in the anaerobic digester. In one embodiment, this combination of ammonia, phosphorus and magnesium will occur in a fluidized bed reactor, creating pellets of struvite. More particularly, the influent to the pellet reactor will be at least a fraction of permeate from the SLS system, with the remaining permeate being directed to the ethanol production process. The effluent from the pellet reactor may be returned to the anaerobic digester, reducing the concentration of ammonia in the digester so that the level is not inhibitory. The respective amounts of ammonia to be treated by the pellet reactor and to be directed to the ethanol production process can be determined based on the actual and desired concentrations of ammonia in the digester. The struvite pellets generated by the pellet reactor have the chemical formula $Mg(NH_4)(PO_4)$. The pellets may be useful as fertilizers with an N:P:K ratio of 5:28:0.

In some independent aspects and in some constructions, the present invention may provide a method of controlling the ammonia levels in the digesters using a fluidized bed of material. Specifically, the method may comprise contacting liquid from the digester with a seed material in a bed of grains of the seed material, while introducing reagents so as to have a substantially complete heterogeneous nucleation take place on the seed material. The bed may be fluidized and kept in fluidization by a liquid stream. In some embodiments, the liquid from the digester contacting the seed material will be permeate from the SLS system. An example of a fluidized bed reactor may be found in U.S. Pat. No. 4,389,317, the entire contents of which are hereby fully incorporated by reference. Another example of a fluidized bed reactor may be found in co-owned, co-pending U.S. Patent Application No. 61/142,295, the entire contents of which are hereby fully incorporated by reference.

A process for chemical reduction of the ammonia content of water may also be provided by adding at least one reagent which forms the crystalline difficultly soluble salt struvite, having the chemical formula $Mg(NH_4)(PO_4)$, and contacting the liquid reagent with a seed material promoting the crystallization. The contacting may take place in a bed of grains of the seed material promoting the crystallization fluidized and kept in fluidization by the liquid stream.

FIG. 4 illustrates one possible embodiment of a struvite removal process. This embodiment is particularly adept at removing ammonia. The treatment process may include feeding at least a fraction of the permeate 4-1 containing the ammonia to the fluidized bed pellet reactor 4-6. In the fluidized bed reactor 4-6, the chemical reagent 4-2 in a storage container 4-4 may be introduced on a continuous basis. After leaving the fluidized bed reactor 4-6, the treated permeate 4-7, with low ammonia concentration, is returned to the anaerobic digester, diluting the ammonia concentration in the digester. Seed material 4-3 may be fed to the fluidized bed reactor 4-6 on a periodic basis. A seed feed vessel 4-5 may be used to introduce the seed material into the fluidized bed reactor 4-6. Pellets 4-8 may be discharged from the fluidized bed reactor 4-6 on a periodic basis. The pellets 4-8 may be drained and stored in a pellet container 4-9.

The fluidized bed pellet reactor 4-6 may be used to treat the permeate 4-1 containing excess ammonia as well as magnesium and phosphate by crystallizing struvite onto seed material 4-3. The fluidized bed 4-6 keeps the pellets 4-8 and seed material 4-3 in a constant state of suspension (fluidization) to mix the permeate 4-1, the seed material 4-3, and the chemical reagent 4-2 to promote crystallization of the ammonium, magnesium, and phosphate on the seed material 4-3. The seed material 4-3 may be fed to the fluidized bed reactor 4-6 to provide the required substrate to which the crystallization occurs. The reagent 4-2 may be introduced near the bottom of the reactor 4-6 with nozzles to further promote mixing. The chemical reagent 4-2 may be selected based on the permeate 4-1 quality, the desired treated permeate 4-7 quality, and/or the desired pellet 4-8 quality. The pellet container 4-9 may be used to both store the pellets 4-8 formed in the fluidized bed 4-6 and drain away permeate 4-1 that may have accompanied the pellets 4-8 during removal.

The pH within the fluidized bed reactor is controlled by dosing an appropriate chemical reagent. In some embodiments, this may be a basic chemical reagent. The pH in the fluidized bed reactor may be at least about 8.0, and more suitably at least about 8.5. The pH may also be less than about 9.5, and more suitably less than about 9.0.

An engineered seed material may be used in the fluidized bed. Examples of engineered seed materials may include, without limitation, natural sands, mineral pellets produced using pellet reactor technology, chemically modified sands or mineral pellets, synthetic materials, and combinations thereof. Natural sands of any composition, for example, without limitation, quartz, limestone, dolomite, sea shells, etc, may be used as seed materials. Mineral pellets produced using pellet reactor technology include, but are not limited to, calcium carbonate ($CaCO_3$), calcium phosphate ($Ca_3(PO_4)_2$), magnesium phosphate ($Mg_3(PO_4)_2$), struvite ($NH_4Mg\ PO_4$), and combinations thereof. Chemically modified sands or mineral pellets may be, without limitation, sands or mineral pellets treated with chemical coatings and/or chemical functionalization designed to enhance the effectiveness of the sands as seed material. Synthetic materials may include, without limitation, silica gels, aluminas, zeolites, chemically modified derivatives of these materials, and combinations thereof. Selection of the seed material will be dependent on the water characteristics. In particular, the ammonia, magnesium and phosphate concentrations within the digester will affect the defined parameters of preferred seed material and seed size. The desired struvite removal will also affect the defined parameters of the seed material and seed size.

The process may include adding at least one reagent which forms a crystalline difficultly soluble salt to the fluidized bed reactor. A reagent(s) may be introduced into the water before it enters the fluidized bed, into the fluidized bed itself, or both. The location of the introduction of the reagent may be dependent on the particular reagent. In one example, at least one reagent is introduced directly into the fluidized bed. In some embodiments, this may be the last reagent added. In other embodiments, at least one reagent may be introduced into the water before it enters the fluidized bed. This introduction of a reagent may be referred to as chemical dosing.

Examples of reagents which may be used include, without limitation, $Mg(OH)_2$, NaOH (about 5 to about 50%, suitably about 25 to about 50%), $MgCO_3$, $MgCl_2$, and combinations thereof. Reagent dosing rates will depend on reagent concentrations, volume of liquid treated and required removal rate. For maximum removal, a small excess above the required stoichiometric amount of added reagent (about 5 to about 10%) will be required. Due to cost and product quality considerations, it may not be preferred to maximize removal. This is best evaluated on a case by case basis to determine the most advantageous reagent dosing levels.

Because of the accretion of the crystalline struvite on the grains of the fluidized bed these grains increase in size and weight and the weight of the bed increases. This causes the minimum fluidization velocity to rise. If this minimum fluidization velocity reaches the value of the current velocity used, the fluidized bed ceases to exist. Therefore, the largest particles are periodically removed from below in the reactor. In order to keep the number of particles more or less constant in the reactor, fresh seed particles are added in the upper region of the reactor.

The pellets produced may contain about 70 to about 95 wt % struvite lattice with about 5 to about 30 wt % that may be seed material, moisture, and trace materials that may become incorporated in the pellet. In some cases the struvite lattice may be about 95 to about 100% when struvite is utilized as the engineered seed.

In other embodiments, other methods may be used to prevent ammonia from building up in the anaerobic digester where it is inhibitory at levels greater than about 3000 mg/L. These may include, without limitation, reducing the amount of permeate being directed back to the ethanol production process, disposal of excess ammonia, other ammonia removal treatments, and combinations thereof.

In addition, a thin stillage evaporator is not required (although it may additionally be used), which also may result in cost savings.

Figure 1:
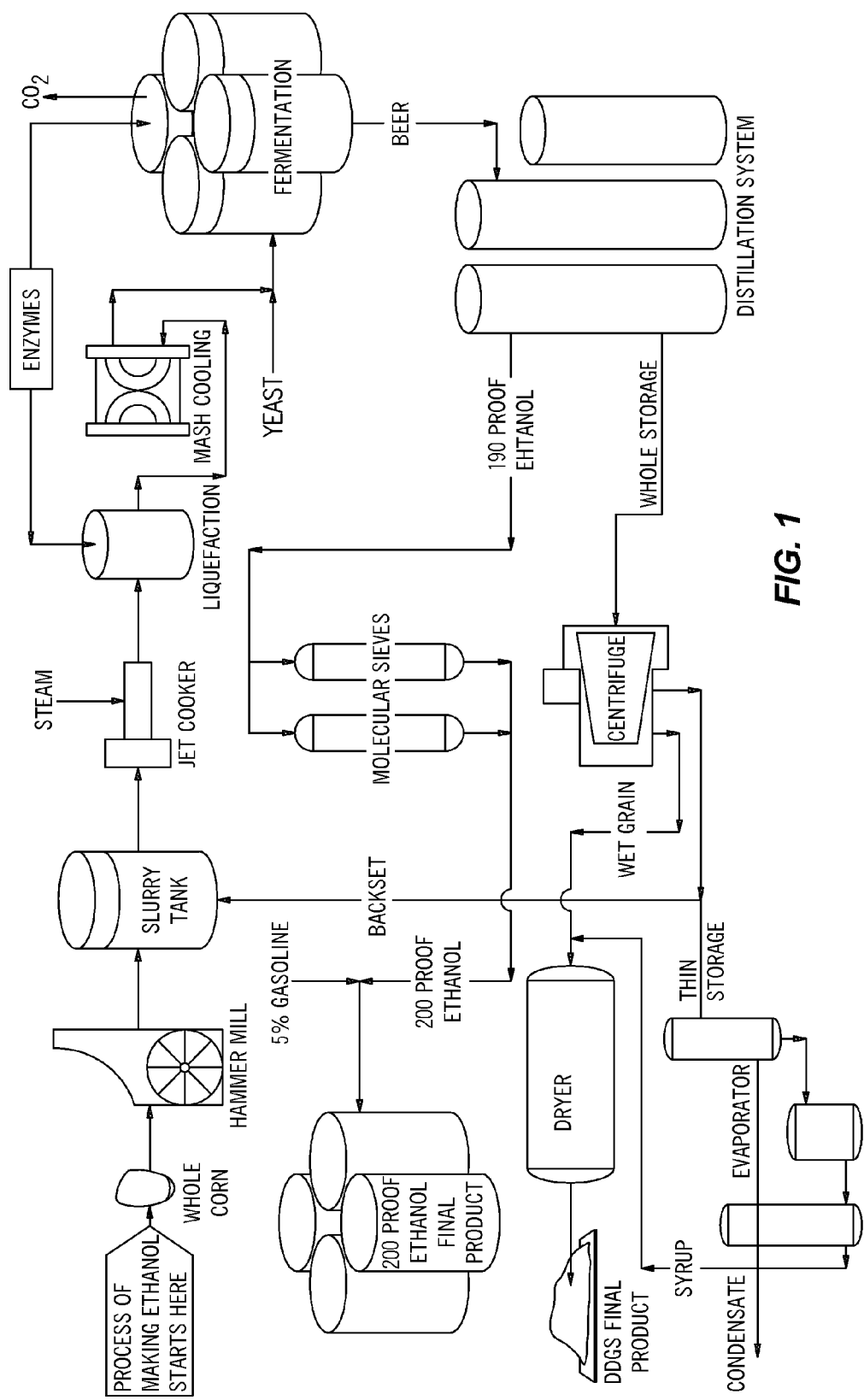
FIG. 1 is a schematic illustration of a traditional ethanol production process and system, excluding anaerobic treatment for thin stillage.

FIG. 1 is a schematic illustration of an ethanol production process. FIG. 1 includes a thin stillage stream emerging from a centrifuge. A portion of the thin stillage stream may return to the slurry tanks and is labeled as backset. A portion of the thin stillage stream may enter an evaporator which produces condensate and syrup. The syrup stream is combined with the wet grain stream and dried to create DDGS.

FIG. 2 is a schematic illustration of an ethanol production process and system including an anaerobic treatment process. FIG. 2 includes a thin stillage stream emerging from a centrifuge. Part of the thin stillage stream may enter a redundant evaporator, which produces condensate and syrup. All or a portion of the thin stillage stream may enter an anaerobic treatment process. FIG. 2 also includes a solid liquid separation system ("SLS") and Struvite Recovery system. FIG. 2 also includes a Flare and Gas Treatment system that are connected to a Boiler.

Figure 3:
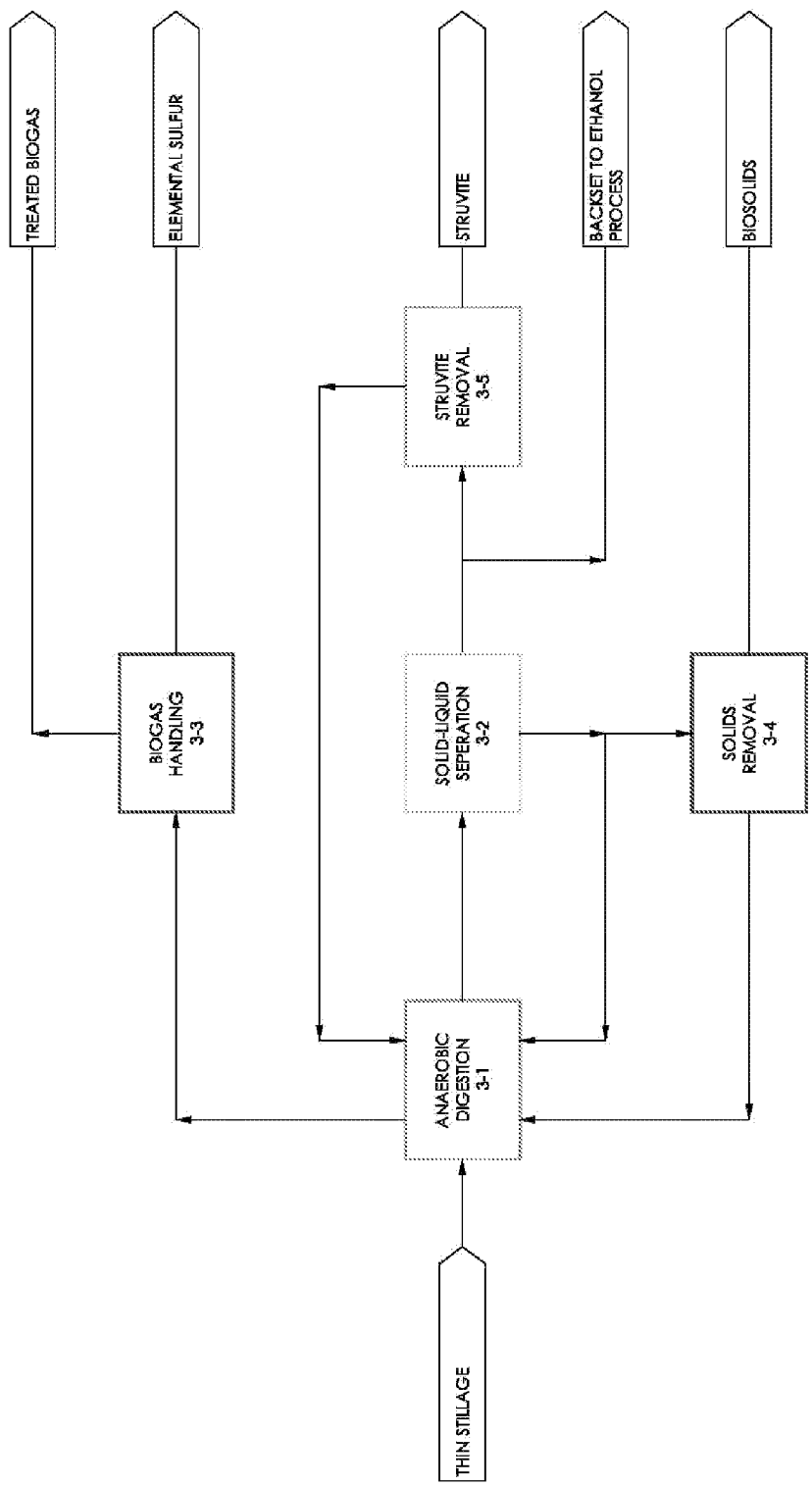
FIG. 3 is a schematic illustration of an anaerobic treatment process of thin stillage

FIG. 3 is a schematic illustration of an anaerobic digester. The process includes five major subsystems: anaerobic digester (3-1), solids-liquid separation system ("SLS") (3-2), biogas handling system (3-3), solids removal system (3-4), and struvite removal system (3-5).

FIG. 4 is a schematic illustration of a struvite recovery subsystem for an Anaerobic Thin Stillage Digester System using a fluidized bed reactor.

FIG. 5 is a schematic illustration of a pilot scale anaerobic digester.

FIG. 6a is a chart summarizing pilot reactor operational parameters during Biomass Building Phase 1, Example 2. Parameters summarized are Added Caustic, pH, and COD Feed Rate.

FIG. 6b is a chart summarizing additional pilot reactor operational parameters during Biomass Building Phase 1, Example 2. Parameters summarized are Suspended Solids, Gas Production Rate, VA:PA.

FIG. 7a is a chart summarizing pilot reactor operational parameters during Biomass Building Phase 2, Example 3. Parameters summarized are pH and COD Feed Rate.

FIG. 7b is a chart summarizing additional pilot reactor operational parameters during Biomass Building Phase 2, Example 3. Parameters summarized are Suspended Solids, Gas Production Rate, VA:PA.

FIG. 8a is a chart summarizing pilot reactor operational parameters during Sustained Operation, Example 4. Parameters summarized are pH and COD Feed Rate.

FIG. 8b is a chart summarizing additional pilot reactor operational parameters during Sustained Operation, Example 4. Parameters summarized are Suspended Solids, Gas Production Rate, VA:PA.

Figure 9A:
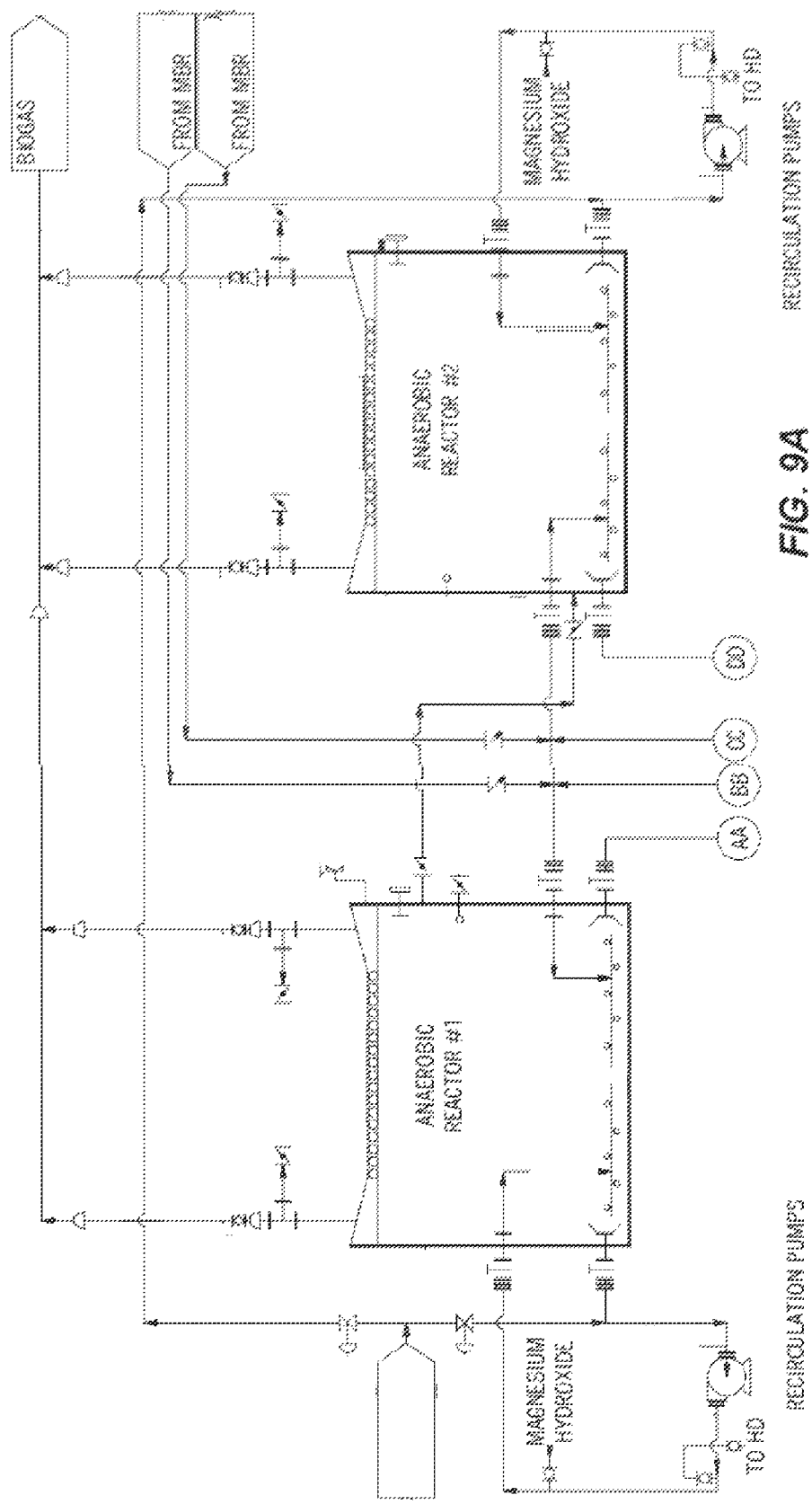
FIG. 9 is a schematic illustration of part of an anaerobic digestion process and system for thin stillage at an ethanol production plant, such as in Example 5.
Figure 9B:
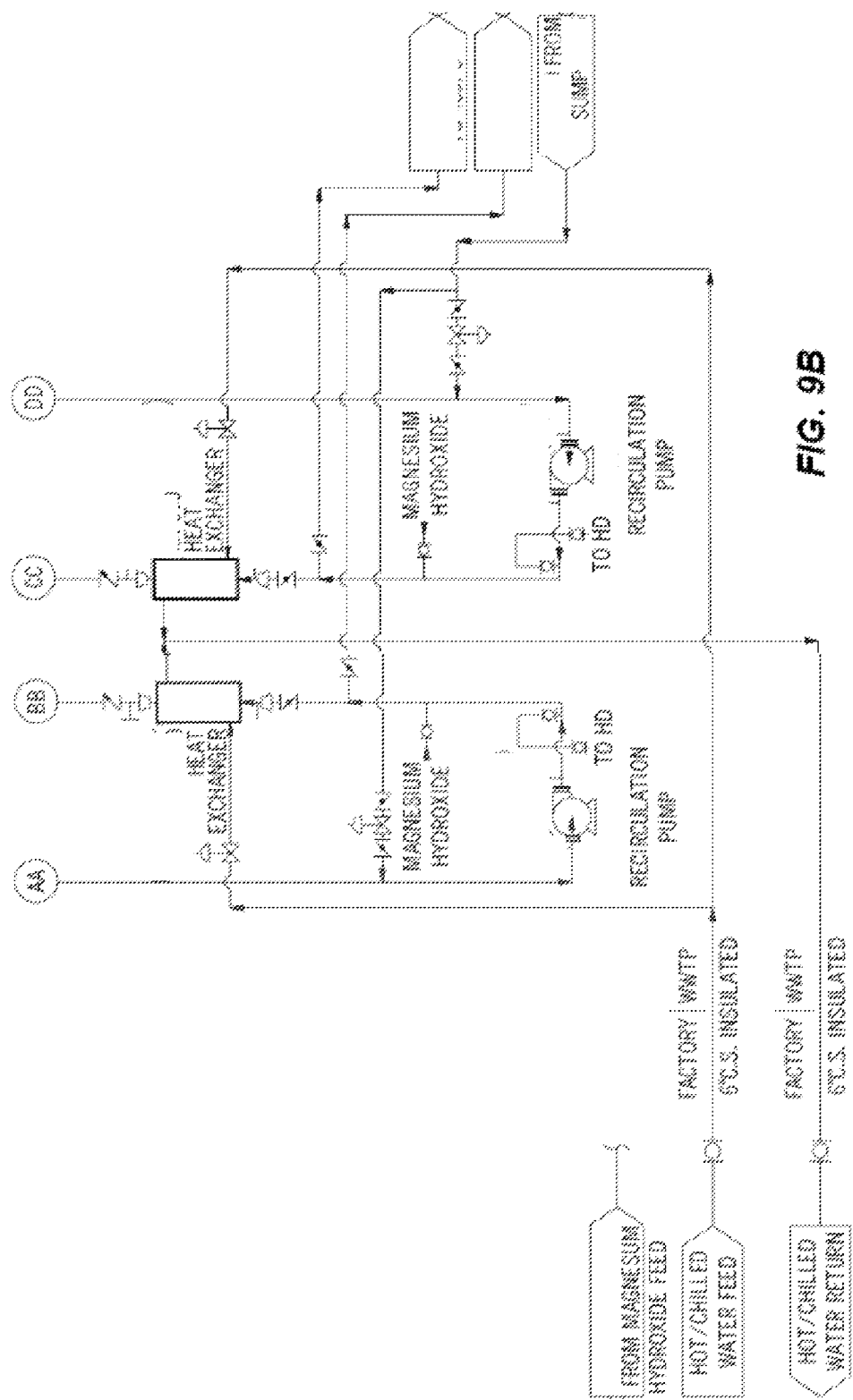

FIG. 9 is a schematic illustration of part of an anaerobic digestion process and system for thin stillage at an ethanol production plant, such as in Example 5. FIG. 9 includes two anaerobic reactors. FIG. 9 also includes heat exchangers, recirculation pumps, hot/chilled water feed and return, and various others components and instruments that are part of the digestion process.

Figure 10:
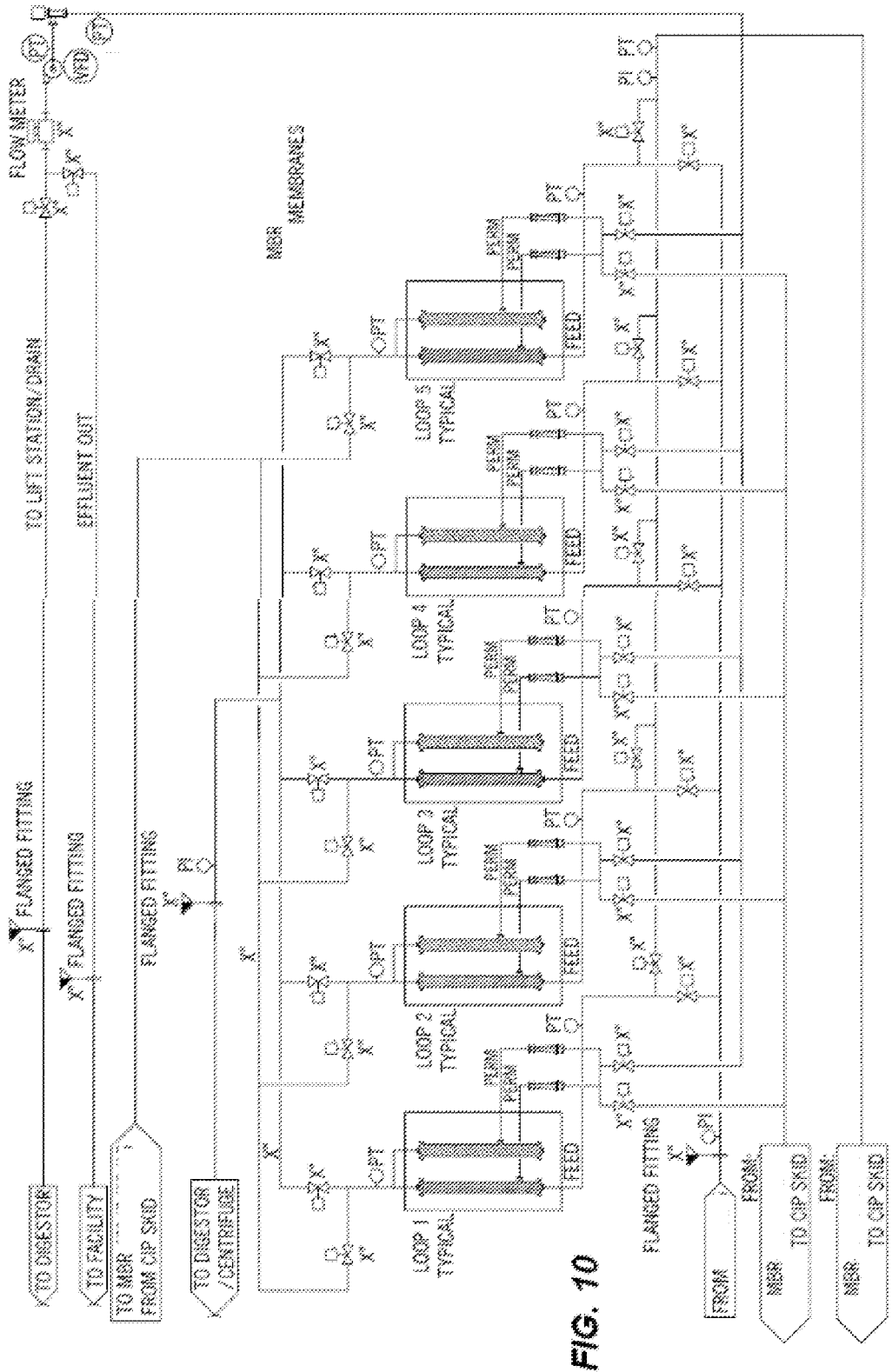
FIG. 10 is a schematic illustration of part of an anaerobic digestion process and system for thin stillage at an ethanol production plant, such as in Example 5.

FIG. 10 is a schematic illustration of part of an anaerobic digestion process and system for thin stillage at an ethanol production plant, such as in Example 5. FIG. 10 includes a flow meter, membranes, and various other components and instruments that are part of the digestion process.

Figure 11:
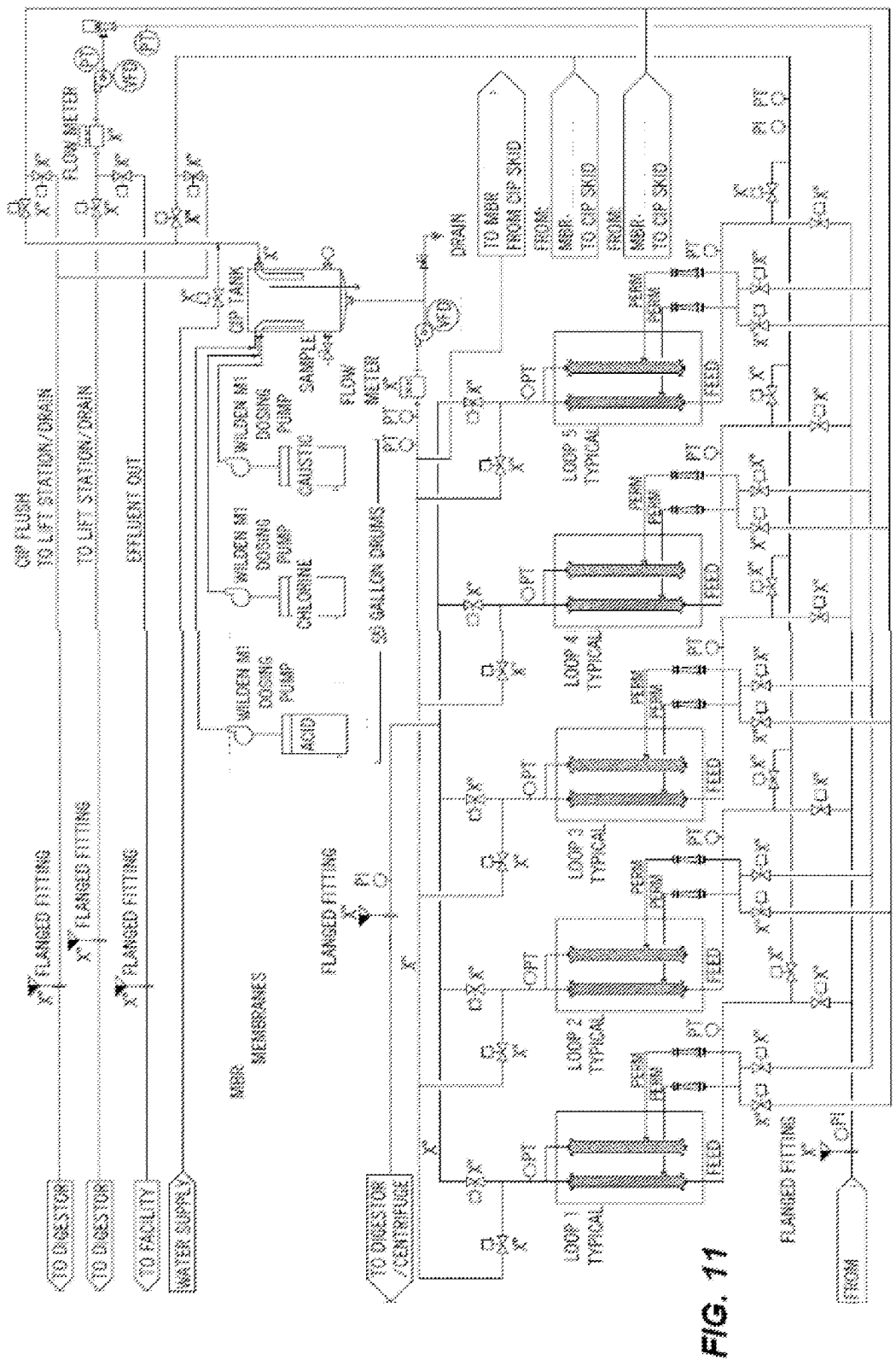
FIG. 11 is a schematic illustration of part of an anaerobic digestion process and system for thin stillage at an ethanol production plant, such as in Example 5.

FIG. 11 is a schematic illustration of part of an anaerobic digestion process and system for thin stillage at an ethanol production plant, such as in Example 5. FIG. 11 includes flow meters, a lift station/drain, an acid tank, a chlorine tank, a caustic tank, dosing pumps, a CIP tank, membranes, and various other components and instruments that are part of the digestion process.

Figure 12:
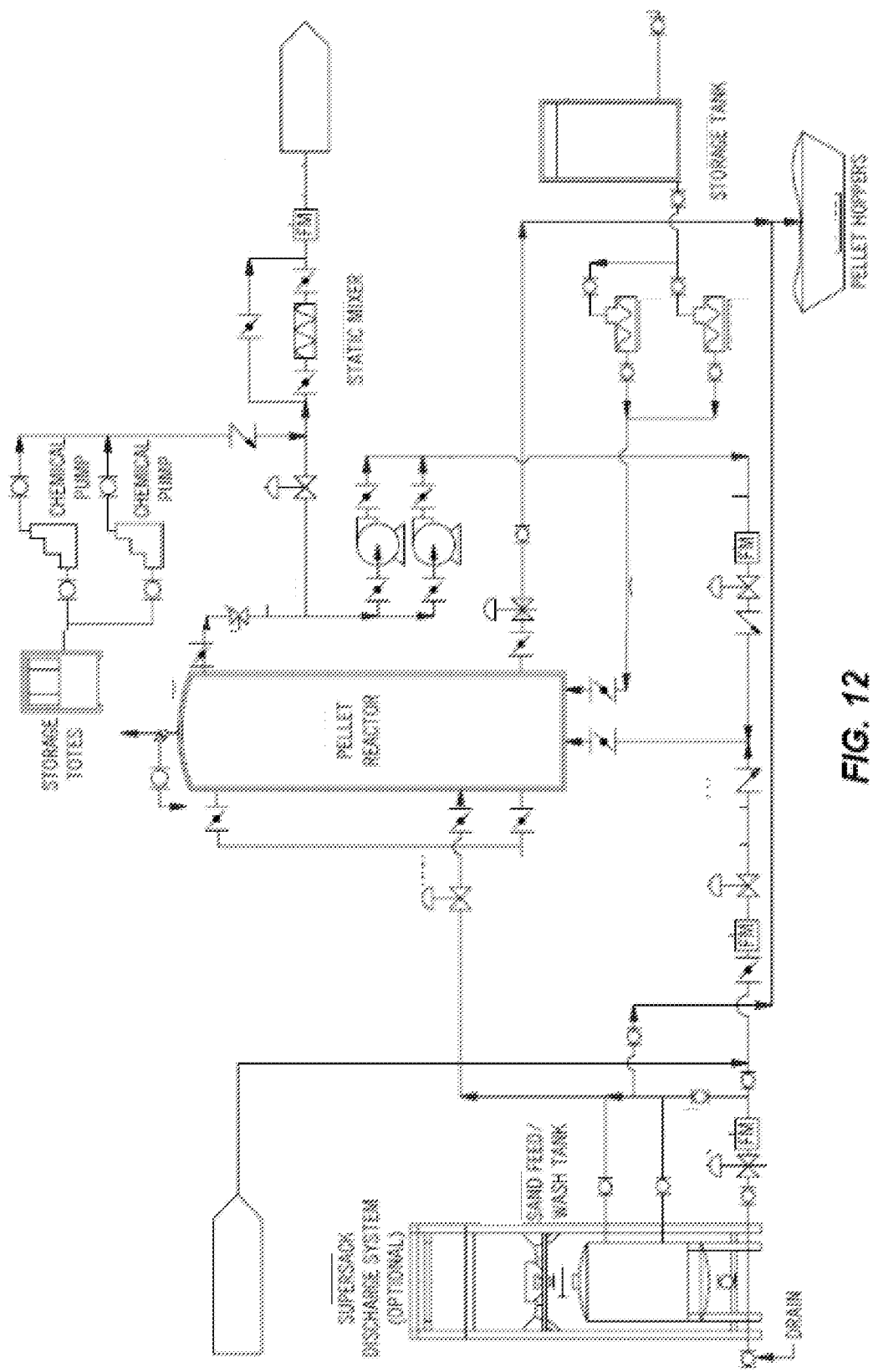
FIG. 12 is a schematic illustration of part of an anaerobic digestion process and system for thin stillage at an ethanol production plant, such as in Example 5.

FIG. 12 is a schematic illustration of part of an anaerobic digestion process and system for thin stillage at an ethanol production plant, such as in Example 5. FIG. 12 includes a Supersack Discharge System, a pellet reactor, recirculation pumps, chemical pumps, storage tanks, pellet hoppers, and various other components and instruments that are part of the digestion process.

Figure 13A:
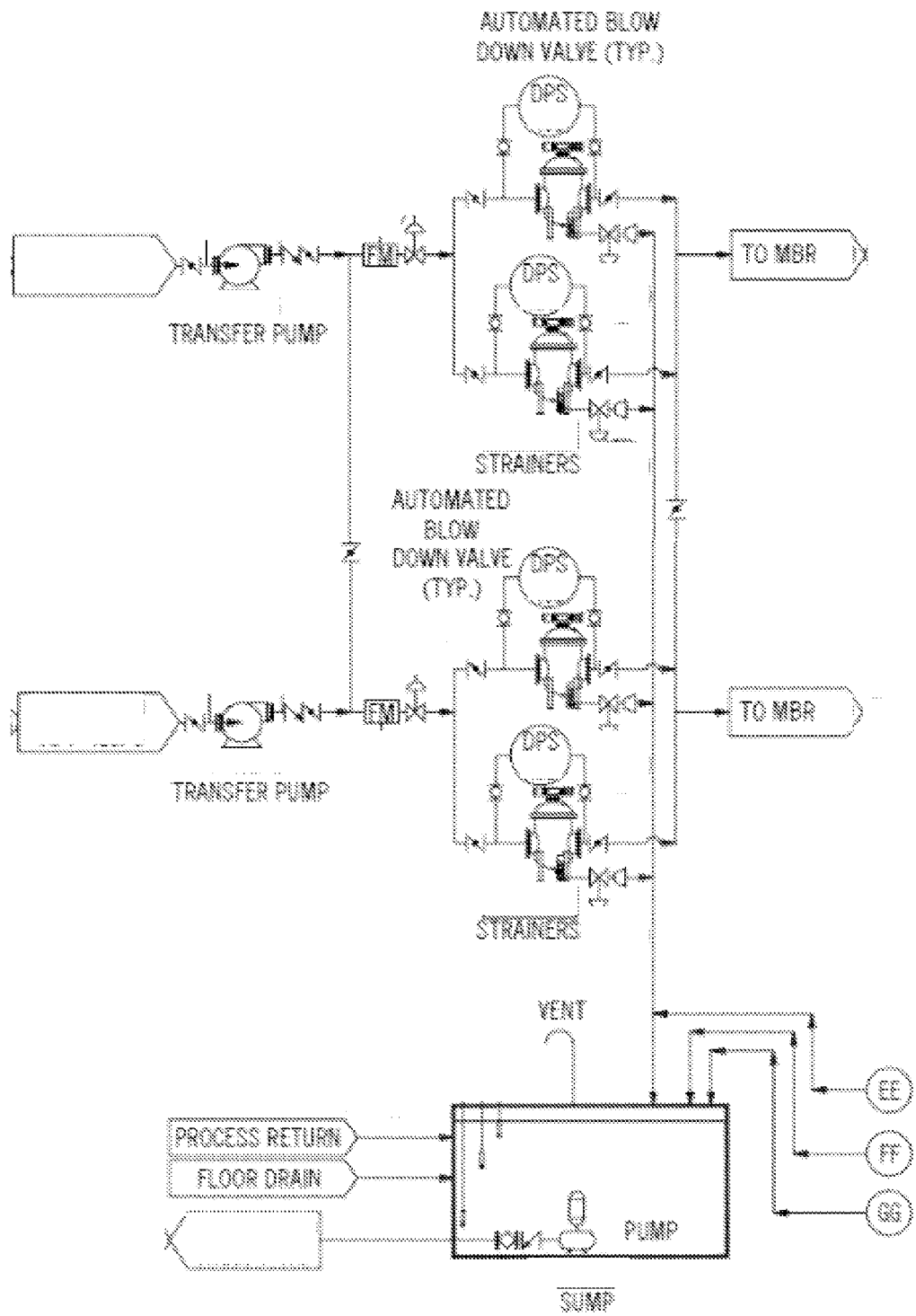
FIG. 13 is a schematic illustration of part of an anaerobic digestion process and system for thin stillage at an ethanol production plant, such as in Example 5.
Figure 13B:
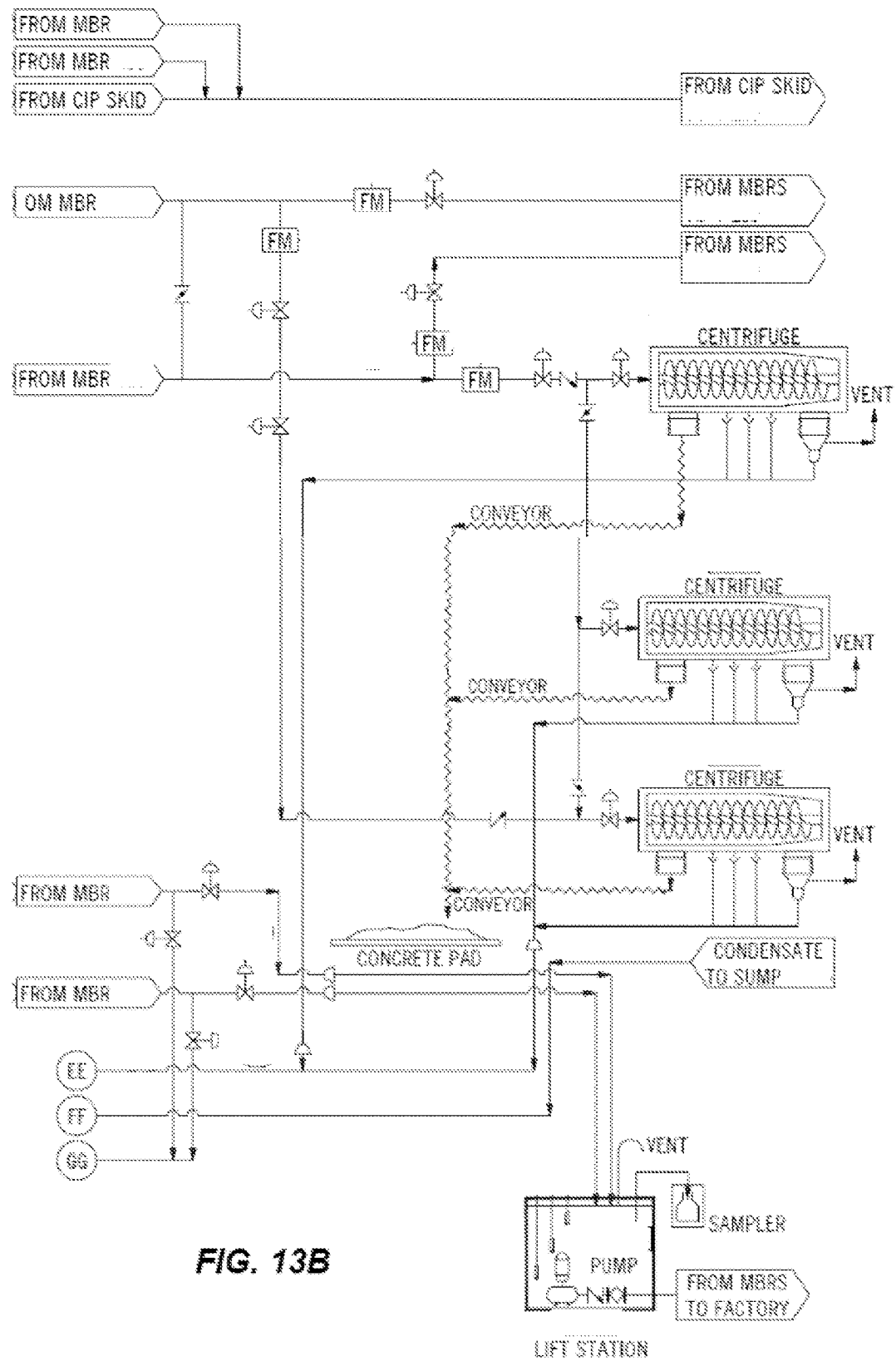

FIG. 13 is a schematic illustration of part of an anaerobic digestion process and system for thin stillage at an ethanol production plant, such as in Example 5. FIG. 13 includes transfer pumps, strainers, sumps, polymer storage tank, polymer transfer pump, polymer day tanks, centrifuges, conveyors, concrete pads, life stations, samplers, floor drains, and various other components and instruments that are part of the digestion process. FIGS. 10 and 11 are inserted into the schematic of FIG. 13 at the "Sheet 3A and 3B" location.

Figure 14:
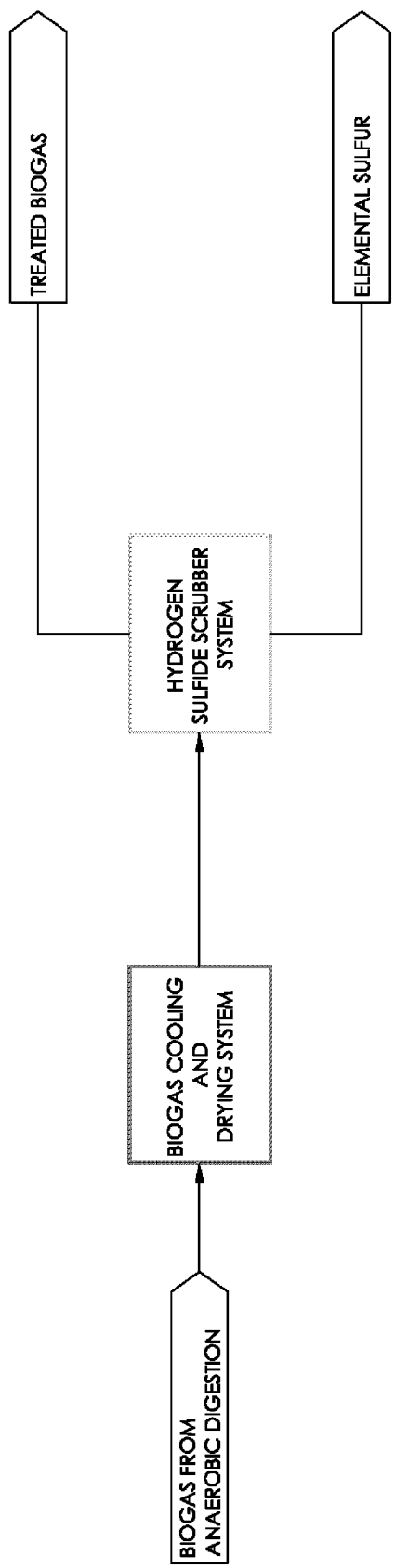
FIG. 14 is a schematic illustration of part of an anaerobic digestion process and system for thin stillage at an ethanol production plant, such as in Example 5.

FIG. 14 is a schematic illustration of part of an anaerobic digestion process and system for thin stillage at an ethanol production plant, such as in Example 5. FIG. 14 is a biogas handling system and includes a collection system, drying and cooling system, a biological hydrogen sulfide scrubbing system, and various other components and instruments that are part of the digestion process.

In some independent aspects and in some constructions, the present invention may enhance the starch to ethanol yeast conversion and improve ethanol production yield. In some independent aspects and in some constructions, the present invention may result in energy saved and the elimination of carbon dioxide. For instance, a normal ethanol plant may require 1 energy unit to produce 1.24 energy units. In some independent aspects and in some constructions, the present invention may enable an ethanol plant to put in 1 energy unit to produce about 1.6 energy units. Ethanol plants also use large amounts of water. In some independent aspects and in some constructions, the present invention may reduce the water usage by about 0.5 million gallons/day. In some embodiments, this may result in reducing the amount of water consumed by about 50%.

In some independent aspects and in some constructions, the present invention may perform better than conventional anaerobic, aerobic, and reverse osmosis processes. For instance, it may generate about 1.67 times the renewable energy (about 4,770 versus about 2,860 dekatherms/day). It may produce water quality with less total solids (about 1-2% versus about 4% in the dissolution tank). It may supply ammonia back to the fermentation process, which may enhance the process. It may eliminate brine water associated with the RO system (about 200,000 gallons per day). It may mitigate start-up and operational risks. It may result in total operating savings of approximately $8 to $10 million/year (excluding less energy consumption). In some independent aspects and in some constructions, the present invention may also improve the return on investment by approximately $8.7 million/year.

EXAMPLES

Exemplary embodiments of the present invention are provided in the following examples. The following examples are presented to illustrate the present invention and to assist one of ordinary skill in making and using the same. The examples are not intended in any way to otherwise limit the scope of the invention.

Example 1

Pilot Scale Digester

A pilot scale anaerobic digestion system shown in FIG. 5 was installed at the Renew Energy Ethanol Plant (REEP) in Jefferson Wis. The pilot unit was used to digest thin stillage generated at REEP.

The pilot unit consisted of the anaerobic digester (1). The digester was a sealed drum, with an operating capacity of about 40 gallons, it was equipped with a draft tube (2) to allow for over-pressure release. The digester was also equipped with a thermal well and digital thermometer (3) for monitoring temperature, a calibrated sight tube for monitoring liquid level in the digester (4). A fitting at the top of the digester was connected to flow meter (5) for measurement of the biogas production rate; after the meter the biogas was vented outside. An additional port (6) on top of the reactor was used to sample the biogas for composition. A fitting at the bottom was connected to centrifugal pump (7) which supplied the ultra filtration membrane (8). Retentate (9) from the membrane passed through a heat exchanger (10) and was returned to the digester via a nozzle (11) at the bottom of the digester; the nozzle provided continuous mixing of the digester contents. Permeate from the membrane (12) was either returned to the digester via return line (13) or wasted via line (14). Thin stillage was fed into the digester using a diaphragm pump (15).

The digester was also equipped with a pH control system. This system included a pH probe (16) between pump 7 and membrane 8, a pH control unit (17) with relays to activate pumps for controlling the pH. The meter's low pH relay was connected to a peristaltic pump (18) which pumped dilute caustic (5% NaOH) into the reactor whenever the pH dropped below the set point.

The digester was monitored every 1 to 2 days as needed. Measurements recorded were temperature, level, total biogas flow, biogas composition (% $CH_4$, % $CO_2$, % $O_2$, balance) membrane pressure, weight of thin stillage fed, weight of permeate wasted, weight of caustic used. In addition samples of permeate and digester mixed liquor were collected. The samples were analyzed for total solids, suspended solids (mixed liquor only), alkalinity (VA and PA, permeate only) and COD. Fresh thin stillage was collected and sampled for measurement of total solids and COD; the in use thin stillage was discarded and replaced with the fresh thin stillage.

The digester was operated at a temperature of 95±3 F, and a level of about 40 gallons; permeate was wasted as need to maintain this level. As discussed in example 2-4 (below), the thin stillage feed rate was determined by the COD in the stillage and the target COD loading rate.

Example 2

Pilot Scale Digester—Biomass Building Phase 1

The first phase of operation of the digester was intended to build biomass rapidly using pH control; this phase lasted about 5 weeks. The pilot scale reactor described in Example 1 was seeded with 5 gallons of biomass from an anaerobic digester (source: cheese plant in Waupun, Wis.); and the level brought to 30 gallons with tap water. The initial suspended solids were about 1500 mg/L. The digester was operated in semi batch mode for 8 days by adding 1 gallon of thin stillage each day. Continuous feeding of thin stillage started on the $9^{th}$ day; basic operation of the digester was as described in Example 1. The average level in the digester during continuous feeding was 39.6±3.5 gallons. The thin stillage feed rate was adjusted for the actual level in the digester and varying COD concentration of the thin stillage with the target COD loading gradually increasing from 1.5 to 3.0 kg/m$^3$/day during the 26 days of continuous operation of Phase 1.

FIG. 6a shows the actual feed rate of thin stillage (in kg/m$^3$/day) for this period. In addition to thin stillage, micronutrients, iron (as an iron chloride solution) and VitaStim (a commercial supplement by Aquafix, Madison Wis.) were added to the digester on a daily basis. On several occasions, the actual rate was quite different from the target rate. For example, on Apr. 30, 2008, the actual loading rate spiked up to 6.11 kg/m$^3$/day, much higher than the target of 1.5 kg/m$^3$/day. Most of these deviations from the target feed rate were attributed to pumping problems; in this case the pump was stuck in prime mode for an excessive time. FIG. 6a also summarizes the pH and caustic (5% NaOH) added to control the pH during this phase of operation. The pH of the digester was stable during the entire period while caustic addition to control pH was essentially unnecessary after May 9, 2008. Note the spike in COD loading on 4/30 was accompanied by a spike in caustic addition.

FIG. 6b shows the values for 3 additional important parameters during this phase of continuous operation. Suspended solids were 3400 mg/L on 4/21 and increased to almost 14,000 mg/L by 5/23. The alkalinity ratio, volatile acid alkalinity (VA) to partial alkalinity (PA), started this phase at almost 1.5, but was just slightly over 0.5 by the end. The gas production rate (in cubic feet/pound COD destroyed/day=cf/lb/d) generally increased during the period. Gas production averaged 7.04 cf/lb/d for the first 4 days of the period and 11.3 for the last 4 days. Gas composition (not shown) was fairly consistent over the period with methane comprising 62±5% of the gas for the period.

By the end of phase 1 of biomass building operation, the suspended solids in the digester had increased nearly 10 fold and the use of pH control was no longer need to maintain ecological balance between the different organisms making up the biomass. Stress events, like the one day boost in COD loading on 4/30 help to develop a robust biological community capable of digesting thin stillage.

Example 3

Pilot Scale Digester—Biomass Building Phase 2

The second phase of operation of the digester was intended to continue building biomass rapidly but without pH control; this phase lasted about 5 weeks. The average level in the digester during continuous feeding was 37.4±5.2 gallons. The thin stillage feed rate was adjusted for the actual level in the digester and varying COD concentration of the stillage with the target COD loading gradually increasing from 3.0 to 5.25 kg/m$^3$/day during the 35 days of continuous operation of Phase 2.

FIG. 7a shows the actual feed rate of thin stillage (in kg/m$^3$/day) for this period. Addition of micronutrients was stopped during this period. On 6 days the actual rate was zero due to pumping problems; there were no incidents in which the feed rate was much higher than the target rate. FIG. 7a also summarizes the pH during this phase of operation. The pH of the digester was fairly stable during the entire period, with an average value of 7.47±0.12.

FIG. 7b shows the values for 3 additional important parameters during this phase of continuous operation. Suspended solids were about 15,000 mg/L on 5/24 and increased to about 24,000 mg/L by the end of this phase of biomass building. The alkalinity ratio, volatile acid alkalinity (VA) to partial alkalinity (PA), started this phase at 0.5, and decreased to about 0.3 by the end. The gas production rate was fairly constant during the period with an average of 10.0±2.2 cf/lb/d. Data for this value is not presented for the days when thin stillage feed was zero due to difficulties estimating COD destroyed. Gas composition (not shown) was fairly consistent over the period with methane comprising 58.8±5.5% of the gas for the period.

By the end of phase 2 of biomass building operation, the suspended solids in the digester had increased an additional 60% and the target COD loading was 95% of the 6 kg/m$^3$/day goal for sustained digestion of thin stillage.

Example 4

Pilot Scale Digester—Sustained Operation

The sustained operation phase of the pilot digester study was intended to provide information relating to several issues regarding thin stillage digestion. First, it was intended to demonstrate that thin stillage loading rates of at least 6 kg/m$^3$/day could be achieved for a long period. Second it was intended to verify full scale digester design and production parameters, such as methane production rate, hydrogen sulfide production rate, and ammonia concentrations. The sustained operation phase lasted over 13 weeks. The average level in the digester during continuous feeding was 35.5±4.5 gallons. The thin stillage feed rate was adjusted for the actual level in the digester and varying COD concentration of the stillage, the target COD loading was 6.0 kg/m$^3$/day for the first part of this trial, until 9/18; after this date the target was increased to 7.5 kg/m$^3$/day.

Micronutrients (VitaStim only, see Example 2) were added during the first part of this study; the additions started on 7/2 and ended on 7/17. An antifoaming agent was used intermittently, to control foaming during 2 significant foaming incidents. The longest use of antifoaming agent was between 7/29 and 8/19; this foaming problem was eventually traced to loose threaded pipe fittings on the suction side of the circulation pump which was causing aspiration of air into the culture being pumped to the filtration membrane. If the cause of this problem had been determined sooner, less antifoam use would have occurred. Foaming caused a substantial loss of liquid and biomass (see below) in the digester; the minimum level was 28 gallons on 8/16. The second foaming incident occurred on 8/31 causing the digester to level to drop to 20 gallons; this event was caused by a plugged gas exhaust vent which resulted in pressure build up in the reactor.

FIG. 8a shows the actual feed rate of thin stillage (in kg/m$^3$/day) for this period. Due to pumping problems, there were 4 days when the thin stillage feed rate was zero. Average COD loadings were 5.7±1.6 kg/m$^3$/day from the start until 8/9, 5.1±1.8 kg/m$^3$/day from 8/9 until 9/17 when the target was increased to 7.5. From 9/17 until the end, the average COD loading was 7.5±2.0 kg/m$^3$/day.

FIG. 8a also summarizes the pH during this phase of operation. The pH of the digester was fairly stable during the entire period, with an average value of 7.39±0.08. The pH did drop to 6.85 on 8/14 and was at ~7.0 the day prior and for 2 days after the minimum on 8/14. These lower pH values are associated with the first foaming incident (see above) and the resulting loss of biomass (see below). The digester pH was not affected by the second foaming incident.

FIG. 8b shows the values for 3 additional important parameters during sustained digester operation. Suspended solids started the trial at about 25,000 mg/L, but quickly climbed to about 34,000 mg/L. They remained at about this concentration until they started a slow decline caused by the first foaming incident (from 7/29 to 8/19, see above); the lowest suspended solids value during the foaming event was 18,500 on 8/18. They hovered around 20,000 mg/L until a few days after the second foaming incident on 8/31; from 9/5 to 9/10 the suspended solids dropped to 12,000 due to dilution of biomass as the digester volume was increased from the minimum level of 20 gallons to 33 gallons. Continued level increases over the next three days, the level returned to 40 gallons on 9/13, were matched by growth of biomass and therefore fairly steady suspended solids. Biomass continued to recover and by 9/27 suspended solids were back in the range of about 25,000 mg/L and still increasing. The mean suspended solids concentration for the last 20 days of operation (10/1 to 10/20) was 27,000±9,000.

The alkalinity ratio, volatile acid alkalinity (VA) to partial alkalinity (PA), was affected by the foaming incidents. Measurements were not done during part of the first incident; when they were resumed the ratio had increased to about 0.66 remaining at about this level until about 8/31. Prior to the foaming incidents the alkalinity ratio was 0.27±0.1, and after recovering it was 0.32±0.2.

The ammonia concentrations in both the digester and permeate were measured on Jul. 29, 2008 to be 1600 and 1200 mg as nitrogen/L respectively. Ammonia in permeate was also measured on Oct. 7, 2008; it was 1600 mg/L as nitrogen.

The gas production rate was also affected by the foaming incidents; there were 2 minima associated with these incidents on 8/12 and 9/4. Prior to the foaming incidents the average gas production was 9.2±0.8 cf/lb/d, with a methane concentration of 56.5±2.6%. After recovering, gas production was 11.8±2.2 cf/lb/d, with a methane concentration of 53.5±9.6%. Hydrogen sulfide in the biogas, measured on Oct. 7, 2008, was 1900 mg/L.

The sustained operation phase of the pilot digester study demonstrated that a robust biomass had been established in the anaerobic digester. The system was able to recover from a significant foaming event rapidly; even higher than originally targeted thin stillage loading rates (7.5 kg/m$^3$/day) were achieved after the recovery. It is clear that anaerobic digesters can be sustainably operated with thin stillage loading rates of at least about 5-7.5 kg COD/m$^3$/day, and probably even higher. Biogas production rates ranged from 9.2-11.8 cf/lb/d with concentrations of methane of 56.5 and 53.5% respectively; these values convert to methane production rates of 5.2-6.3 cf/lb/d.

Example 5

Prophetic Full Scale Thin Stillage Digestion System

An ethanol plant with a capacity of 130 million gallons per year produces 992,000 gallons of thin stillage per day. The thin stillage is 87 percent moisture (by weight) with a COD value of 97,200 mg/L; this equates to 804,000 pounds per day of COD in the thin stillage.

All of the thin stillage from an ethanol plant is anaerobically digested (FIG. 2). The anaerobic digester volume is based on 7 kg COD destroyed per cubic meter per day average. There are two anaerobic digester tanks (FIG. 9), each with a diameter of 200 feet and a height of 30 feet (7.05 Mgal or 26,700 cubic meters). The anaerobic digester is a completely mixed tank to provide increased contact between the bacteria and the thin stillage.

The digester is completely mixed through the use of recirculation pumps that draw the digester contents and pump them through jet mixing nozzles. Four (4) 100-hp centrifugal pumps are dedicated to keeping the tank well-mixed. The temperatures of these tanks are maintained at 90 to 95 degrees Fahrenheit through the use of shell-and-tube heat exchangers using cooling water.

The anaerobic digester is a completely mixed tank that includes an integrated solid-liquid separator (SLS). The type and size of SLS is evaluated and for this ethanol plant is determined to be an ultrafiltration (UF) membrane (FIGS. 10 and 11). The UF membrane system is installed and is capable of processing 1 million gallons per day of permeate. The anaerobic mixed liquor is processed at 12,000 gallon per minute at a 5 percent recovery. The recovery is very low to keep the membranes from fouling and building up anaerobic solids within the membrane tubes. The retentate that is returned to the digester is forced through a jet mixing system which aids in keeping the digester tanks completely mixed to provide increased contact between the bacteria and the thin stillage.

The permeate from the UF membrane is split and either returned to the anaerobic digester (by way of a sump) or sent back to the ethanol process as backset based on the level in the digester tanks.

The permeate contains a high concentration of ammonia which is beneficial to the ethanol process. All of the permeate produced from the anaerobic digester is backset to the ethanol process and offsets nearly 1 million gallons per day of water needed in the slurry and liquefaction tanks. The ammonia that is in the permeate averages 1200 mg/L as N, which equates to 12,000 pounds of ammonia per day. This offsets 12,000 pounds per day of ammonia that was required in the liquefaction tanks.

An ammonia control system is installed to keep ammonia from building up in the anaerobic digester where it is toxic at levels greater than 3000 mg/L. The ammonia control system is a fluidized bed reactor (Crystalactor®) that crystallizes ammonia as struvite (magnesium ammonia phosphate). The fluidized bed reactor is installed on a side-stream of the UF permeate where magnesium hydroxide is the treatment chemistry (FIG. 12).

The centrifuges are installed on a side-stream of the UF retentate where the mixed liquor suspended solids are at their highest. The decanter-style centrifuge separates the liquid from the suspended solids so that the solids are removed as a "wet cake" with a moisture content of 50-80 percent (by weight) with the aid of a polymer (FIG. 13). The centrifuges operate to maintain a mixed liquor suspended solids content of 3 percent (by weight).

Anaerobic digestion produces biogas at the rate of 10 cubic feet per pound of COD destroyed at a methane content of 55 percent by volume. For this ethanol plant, at a 95% COD destruction rate, 7.64 million cubic feet of biogas (4.20 million cubic feet methane) is produced from the anaerobic digestion of thin stillage. The energy value of 4.20 million cubic feet of methane is 4, 116 million BTU. At $10 per mmBTU, the biogas from anaerobically digesting the thin stillage is valued at $15M per year.

The biogas is evaluated for energy potential, including, but not limited to, burning for heat or burning for electricity. The strategies of biogas treatment are dependent on the unit process for the utilization of the biogas. These strategies for biogas treatment include, but are not limited to, removal of impurities such as water, sulfur, carbon dioxide, ammonia; compression; pre-heating/cooling; or some combination thereof.

For this ethanol plant, the biogas is used in the previously existing boilers which have been modified to burn biogas (55-65% methane). The 7.64 million cubic feet of biogas is collected, dried, cooled, and scrubbed hydrogen sulfide ($H_2S$) (FIG. 14).

The impurities that can be removed from the biogas are evaluated for reuse potential in the ethanol process and/or salable commodities. The biogas that is delivered to the boiler must be scrubbed of corrosive hydrogen sulfide ($H_2S$). A biological scrubber is installed that removes the hydrogen sulfide as 99 percent pure elemental sulfur (by weight). At the $H_2S$ concentration of 1900 ppm (by volume), the elemental sulfur that is recovered is 1200 pounds per day.

What is claimed is:
1. A method of treating thin stillage from an ethanol production process, the method comprising:
in a digester, treating thin stillage from the ethanol production process using anaerobic digestion to produce an ammonia-rich liquid product;

during anaerobic digestion of the thin stillage, with a solids/liquids separation system of the digester, separating the ammonia-rich liquid product from a mixed liquor to produce a permeate;

recycling at least a portion of the permeate from the solids/liquids separation system of the digester directly to the ethanol production process.

2. The method of claim 1, wherein a secondary treatment step is not used to treat the permeate before recycling it into the ethanol production process.

3. The method of claim 1, wherein the separating step includes separating the ammonia-rich liquid product from the mixed liquor using membrane technology.

4. The method of claim 3, wherein the separating step includes separating the ammonia-rich liquid product from the mixed liquor using at least one of microfiltration, ultrafiltration, nanofiltration, reverse osmosis, and combinations thereof.

5. The method of claim 1, wherein the recycling step includes recycling the permeate directly to the ethanol production process as a substitute for water in one of a liquefaction step, a saccarifaction step, and a combination thereof in the ethanol production process.

6. The method of claim 1, wherein the permeate replaces water in the ethanol production process in a range of about 1% to 100%.

7. The method of claim 1, wherein the permeate replaces from about 1% to about 100% of a nitrogen requirement of the ethanol production process.

8. The method of claim 1, further comprising:
handling biogas produced during anaerobic digestion;
removing solids produced during anaerobic digestion; and
removing ammonia produced during anaerobic digestion including
producing struvite from ammonia, and
removing the struvite.

9. The method of claim 8, and further comprising:
producing biogas;
purifying the biogas to remove $H_2S$ to produce an elemental sulfur byproduct; and
using the biogas for energy in the ethanol production process.

10. The method of claim 8, wherein the digester has a threshold for at least one of ammonia, phosphorus, and magnesium, wherein the method further comprises removing excess of at least one of ammonia, phosphorus, and magnesium above the threshold by processing at least a fraction of the permeate in a fluidized bed reactor to produce pellets of struvite.

11. The method of claim 10, wherein the threshold is 2500 mg/L of ammonia in the digester.

12. The method of claim 1, further comprising providing a mixing system in the digester and mixing contents in the digester with the mixing system.

13. The method of claim 12, wherein the mixing step includes continuously operating the mixing system to continuously mix the contents in the digester.

14. A method for reducing energy required to treat thin stillage from an ethanol production process, the method comprising
combining a solids/liquid separation process in an anaerobic digestion process;
in a digester, treating thin stillage from the ethanol production process using anaerobic digestion to produce an ammonia-rich liquid product;
during anaerobic digestion of the thin stillage, with a solids/liquids separation system of the digester, separating the ammonia-rich liquid product from a mixed liquor to produce a permeate;
recycling at least a portion of the permeate from the solids/liquids separation system of the digester directly to the ethanol production process.

15. The method of claim 14, wherein a secondary treatment step is not used to treat the permeate before recycling it into the ethanol production process.

16. The method of claim 14, wherein the separating step includes separating the ammonia-rich liquid product from the mixed liquor using membrane technology.

17. The method of claim 14, wherein the recycling step includes recycling the permeate directly to the ethanol production process as a substitute for water in one of a liquefaction step, a saccarifaction step, and a combination thereof in the ethanol production process.

18. The method of claim 14, wherein the permeate replaces from about 1% to about 100% of a nitrogen requirement of the ethanol production process.

19. The method of claim 14, further comprising:
handling biogas produced during anaerobic digestion;
removing solids produced during anaerobic digestion; and
removing ammonia produced during anaerobic digestion including
producing struvite from ammonia, and
removing the struvite.

20. The method of claim 19, and further comprising:
producing biogas;
purifying the biogas to remove $H_2S$ to produce an elemental sulfur byproduct; and
using the biogas for energy in the ethanol production process.

21. The method of claim 19, wherein the digester has a threshold for at least one of ammonia, phosphorus, and magnesium, wherein the method further comprises removing excess of at least one of ammonia, phosphorus, and magnesium above the threshold by processing at least a fraction of the permeate in a fluidized bed reactor to produce pellets of struvite.

22. The method of claim 14, further comprising providing a mixing system in the digester and mixing contents in the digester with the mixing system.

* * * * *